United States Patent
Hua et al.

(10) Patent No.: US 12,360,683 B2
(45) Date of Patent: Jul. 15, 2025

(54) OVER-THE-AIR PROGRAMMING OF SENSING DEVICES

(71) Applicant: ABBOTT DIABETES CARE INC., Alameda, CA (US)

(72) Inventors: Xuandong Hua, Mountain View, CA (US); Kurt E. Leno, San Leandro, CA (US); Nelson Y. Zhang, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/869,162

(22) Filed: Jul. 20, 2022

(65) Prior Publication Data

US 2023/0027588 A1    Jan. 26, 2023

Related U.S. Application Data

(60) Provisional application No. 63/249,735, filed on Sep. 29, 2021, provisional application No. 63/224,088, filed on Jul. 21, 2021.

(51) Int. Cl.
*G06F 3/06* (2006.01)
*G11C 16/22* (2006.01)
(Continued)

(52) U.S. Cl.
CPC .......... *G06F 3/0622* (2013.01); *G06F 3/0631* (2013.01); *G06F 3/0634* (2013.01); *G06F 3/064* (2013.01); *G06F 3/0679* (2013.01)

(58) Field of Classification Search
CPC .... G06F 3/0622; G06F 3/0631; G06F 3/0634; G06F 3/064; G06F 3/0679
(Continued)

(56) References Cited

U.S. PATENT DOCUMENTS 4,561,443 A    12/1985    Hogrefe et al.
5,390,671 A    2/1995    Lord et al.
(Continued)

FOREIGN PATENT DOCUMENTS

EP    2 407 094    1/2012
EP    3240352 A1    11/2017
(Continued)

OTHER PUBLICATIONS

International Search Report and Written Opinion mailed Nov. 2, 2022 in International Application No. PCT/US2022/037654.
(Continued)

*Primary Examiner* — Arpan P. Savla
*Assistant Examiner* — Sidney Li
(74) *Attorney, Agent, or Firm* — Baker Botts L.L.P.

(57) ABSTRACT

Embodiments described herein include a sensor control device configured for secure over-the-air (OTA) programming. Embodiments include a sensor control device that includes one or more processors, an analyte sensor, a communication module, and a memory. The memory includes a first set of storage blocks that are in a non-programmable state and a second set of blocks that are in a programmable state. The processors are configured to receive, using the communication module, instructions to write marking data to the memory to mark a first storage block from the first set of storage blocks as inaccessible and to write program data to a second storage block from the second set of storage blocks, causing the second storage block to be placed into the non-programmable state. The program data written to the second storage block includes instructions that cause the processors to process analyte data received from the analyte sensor.

19 Claims, 6 Drawing Sheets

(51) Int. Cl.
  *G11C 17/16* (2006.01)
  *G16H 40/40* (2018.01)

(58) Field of Classification Search
  USPC .......................................................... 711/163
  See application file for complete search history.

(56) References Cited

U.S. PATENT DOCUMENTS

| | | | |
|---|---|---|---|
| 5,482,473 | A | 1/1996 | Lord et al. |
| 5,690,119 | A | 11/1997 | Rytky et al. |
| 6,096,268 | A | 8/2000 | Inbar |
| 6,159,181 | A | 12/2000 | Crossman et al. |
| 6,175,752 | B1 | 1/2001 | Say et al. |
| 6,293,925 | B1 | 9/2001 | Safabash et al. |
| 6,560,471 | B1 | 5/2003 | Heller et al. |
| 6,565,509 | B1 | 5/2003 | Plante et al. |
| 6,689,056 | B1 | 2/2004 | Kilcoyne et al. |
| 6,695,860 | B1 | 2/2004 | Ward et al. |
| 6,728,137 | B1 | 4/2004 | Lin |
| 7,344,500 | B2 | 3/2008 | Talbot et al. |
| 7,643,798 | B2 | 1/2010 | Ljung |
| 8,294,940 | B1 | 10/2012 | McNall et al. |
| 8,401,194 | B2 | 3/2013 | Nierzwick et al. |
| 9,000,914 | B2 | 4/2015 | Baker et al. |
| 9,211,065 | B2 | 12/2015 | Marsh et al. |
| 9,980,140 | B1 | 5/2018 | Spencer et al. |
| 10,375,222 | B2 | 8/2019 | Mandapaka et al. |
| 11,991,175 | B2 | 5/2024 | Rolfe et al. |
| 2003/0050009 | A1 | 3/2003 | Kurisko et al. |
| 2003/0065536 | A1 | 4/2003 | Hansen et al. |
| 2003/0100821 | A1 | 5/2003 | Heller et al. |
| 2003/0144581 | A1 | 7/2003 | Conn et al. |
| 2003/0153900 | A1 | 8/2003 | Aceti et al. |
| 2004/0106860 | A1 | 6/2004 | Say et al. |
| 2004/0117204 | A1 | 6/2004 | Mazar et al. |
| 2004/0122353 | A1 | 6/2004 | Shahmirian et al. |
| 2004/0133164 | A1 | 7/2004 | Funderburk et al. |
| 2005/0027463 | A1 | 2/2005 | Goode, Jr. et al. |
| 2005/0240245 | A1 | 10/2005 | Bange et al. |
| 2005/0242479 | A1 | 11/2005 | Petisce et al. |
| 2005/0261563 | A1 | 11/2005 | Zhou et al. |
| 2005/0283114 | A1 | 12/2005 | Bresina et al. |
| 2006/0016700 | A1 | 1/2006 | Brister et al. |
| 2006/0025663 | A1 | 2/2006 | Talbot et al. |
| 2006/0081469 | A1 | 4/2006 | Lee |
| 2006/0271725 | A1* | 11/2006 | Wong .................. G06F 12/0246 |
| | | | 711/E12.008 |
| 2007/0038044 | A1 | 2/2007 | Dobbles et al. |
| 2007/0060801 | A1 | 3/2007 | Neinast |
| 2007/0073129 | A1 | 3/2007 | Shah et al. |
| 2007/0173710 | A1 | 7/2007 | Petisce et al. |
| 2007/0219480 | A1 | 9/2007 | Kamen et al. |
| 2008/0009805 | A1 | 1/2008 | Ethelfeld |
| 2008/0097246 | A1 | 4/2008 | Stafford |
| 2008/0129486 | A1 | 6/2008 | Jeckelmann et al. |
| 2008/0269687 | A1 | 10/2008 | Chong et al. |
| 2008/0275313 | A1 | 11/2008 | Brister et al. |
| 2008/0278331 | A1* | 11/2008 | Hayter ................ A61B 5/0022 |
| | | | 600/347 |
| 2008/0278333 | A1 | 11/2008 | Fennell et al. |
| 2008/0300476 | A1 | 12/2008 | Stafford |
| 2008/0319145 | A1 | 12/2008 | Yodfat et al. |
| 2010/0045336 | A1* | 2/2010 | Krueger .................. G06F 1/26 |
| | | | 326/38 |
| 2010/0045425 | A1 | 2/2010 | Chivallier |
| 2010/0274218 | A1 | 10/2010 | Yodfat et al. |
| 2011/0072199 | A1* | 3/2011 | Reiter .................... G06F 13/24 |
| | | | 711/170 |
| 2011/0177780 | A1 | 7/2011 | Sato et al. |
| 2011/0213225 | A1 | 9/2011 | Bernstein et al. |
| 2012/0003933 | A1 | 1/2012 | Baker et al. |
| 2012/0123227 | A1* | 5/2012 | Sun ................... A61B 5/14532 |
| | | | 600/309 |
| 2012/0203993 | A1* | 8/2012 | Virgin ................ G06F 12/0246 |
| | | | 711/E12.002 |
| 2013/0297853 | A1* | 11/2013 | Balakrishnan ...... G06F 12/0866 |
| | | | 711/E12.008 |
| 2014/0266776 | A1 | 9/2014 | Miller et al. |
| 2014/0266785 | A1 | 9/2014 | Miller et al. |
| 2014/0273858 | A1 | 9/2014 | Panther et al. |
| 2014/0313052 | A1 | 10/2014 | Yarger et al. |
| 2014/0379273 | A1 | 12/2014 | Petisce et al. |
| 2015/0038818 | A1 | 2/2015 | Cole |
| 2015/0118658 | A1 | 4/2015 | Mayou et al. |
| 2015/0121071 | A1* | 4/2015 | Schwarz .................. H04L 63/12 |
| | | | 713/168 |
| 2015/0123810 | A1 | 5/2015 | Hernandez-Rosas et al. |
| 2015/0164391 | A1 | 6/2015 | Hernandez-Rosas et al. |
| 2015/0205947 | A1 | 7/2015 | Berman et al. |
| 2015/0207796 | A1 | 7/2015 | Love et al. |
| 2016/0055338 | A1* | 2/2016 | Jeansonne ................ G06F 21/56 |
| | | | 726/1 |
| 2016/0086406 | A1* | 3/2016 | Baumgarte ........ G06K 7/10158 |
| | | | 340/5.7 |
| 2016/0165649 | A1 | 6/2016 | Polo et al. |
| 2016/0276043 | A1 | 9/2016 | Chung |
| 2017/0281060 | A1* | 10/2017 | Wedekind ............... A61B 5/742 |
| 2019/0384531 | A1* | 12/2019 | Mitomi .................. G06F 3/0659 |
| 2020/0044868 | A1* | 2/2020 | Vakulenko ............ G06F 21/305 |
| 2020/0104517 | A1* | 4/2020 | Hawkins ............... H04L 9/3273 |

FOREIGN PATENT DOCUMENTS

| | | |
|---|---|---|
| EP | 3 730 045 | 3/2022 |
| WO | WO 99/58190 | 11/1999 |
| WO | WO 02/15778 | 2/2002 |
| WO | WO 03/026728 | 4/2003 |
| WO | WO 2004/006982 | 1/2004 |
| WO | WO 2005/018450 | 3/2005 |
| WO | WO 2005/046780 | 5/2005 |
| WO | WO 2006/040083 | 4/2006 |
| WO | WO 2006/094513 | 9/2006 |
| WO | WO 2006/121921 | 11/2006 |
| WO | WO 2007/097754 | 8/2007 |
| WO | WO 2007/104755 A1 | 9/2007 |
| WO | WO 2008/065646 | 6/2008 |
| WO | WO 2008/073813 | 6/2008 |
| WO | WO 2008/114223 | 9/2008 |
| WO | WO 2008/115409 | 9/2008 |
| WO | WO 2008/144325 A1 | 11/2008 |
| WO | WO 2008/157821 | 12/2008 |
| WO | WO 2009/007287 | 1/2009 |
| WO | WO 2009/035773 | 3/2009 |
| WO | WO 2009/039013 | 3/2009 |
| WO | WO 2013/069894 A1 | 5/2013 |
| WO | WO 2014/145049 A2 | 9/2014 |
| WO | WO 2014/158405 A2 | 10/2014 |
| WO | WO 2014/165172 A1 | 10/2014 |
| WO | WO 2014/179343 | 11/2014 |
| WO | WO 2015/069797 A1 | 5/2015 |
| WO | WO 2015/081268 A1 | 6/2015 |
| WO | WO 2016/064184 A1 | 4/2016 |
| WO | WO 2016/092448 A1 | 6/2016 |
| WO | WO 2016/101774 A1 | 6/2016 |
| WO | WO 2017/172781 A1 | 10/2017 |
| WO | WO 2019/152966 A1 | 8/2019 |
| WO | WO 2022/133308 A1 | 6/2022 |

OTHER PUBLICATIONS

Bluetooth Core Specification v4.0—(Jun. 30, 2010) 89 pgs.
Bluetooth Specification, Version 4.0 [vol. 6], p. 121 of 138, Jun. 30, 2010 (1 page).
U.S. Appl. No. 60/587,787, filed Jul. 13, 2004, Brister et al.
"Within Definition & Meaning" retrieved from "https://www.dictionary.com/browse/within" on Sep. 9, 2022, 5 pages.
Near Field Communication (NFC) Technology and Measurements, White Paper, Rohde & Schwarz, 18 pages (2011).
U.S. Appl. No. 60/614,683, filed Sep. 30, 2004, Brister et al.

(56) References Cited

OTHER PUBLICATIONS

Dowla, "The Basics of Radio Frequency Identification (RFID) Technology", Handbook of RF & Wireless Technologies, Chapter 14, 44 pages (2004).
Evans, et al., "Clinical temperature acquisition using proximity telemetry", J. Biomed. Eng., 13:83-86 (1991).
Finkenzeller, "RFID Handbook: Fundamentals and Applications in Contactless Smart Cards and Identification", Second Edition, 114 pages (2003).
Finkenzeller, "RFID Handbook: Fundamentals and Applications in Contactless Smart Cards, Radio Frequency Identification and Near-Field Communication", Third Edition, 4 pages (2010).
Heller, et al., "Electrochemical Glucose Sensors and Their Applications in Diabetes Management", Chemical Reviews, 108(7):2482-2505 (2008).
Lee, "RFID Coil Design", Microchip Technology Inc., DS00678B, pp. 1-19 (1998).
Liang, et al., "An implantable bi-directional wireless transmission system for transcutaneous biological signal recording", Physiological Measurement, 26:83-97 (2005).
Near Field Communication (NFC) Technology and Measurements, White Paper, Rohde & Schwarz, 1 page (2011).
Radio Frequency Identification RFID, AIM Inc., White Paper, Document Version 1.2, 17 pages (2001).
Sola-Gazagnes, et al., "Emergent technologies applied to diabetes: What do we need to integrate continuous glucose monitoring into daily practice? *Where the long-term use of continuous glucose monitoring stands in 2011*", Diabetes & Metabolism, vol. 37, pp. S65-S70 (2011).
Sorrells, "Passive RFID Basics", Microchip Technology Inc., DS00680B, pp. 1-5 (1998).
Specification of the Bluetooth System, Experience More, Specification vol. 0, Covered Core Package Version: 4.0, 2 302 pages (2010).
Dexcom, Inserting Sensor, Instructions for Use, Dexcom, Inc., 2 pages (2021).
Dexcomg7, Operational Manual, User Guide, Dexcom, Inc., 179 pages (2022) (with an English Abstract).
Dexcomg7, Receiver: Start Here, Operational Manual, Dexcom, Inc., 8 pages (2022).
Dexcomg7, Start Here, Operational Manual, Dexcom, Inc. 9 pages (2022) (with an English Abstract).
U.S. Appl. No. 60/587,787, filed Jul. 13, 2004, 69 pages.
Microchip, microID® 13.56 MHz RFID, System Design Guide, Microchip Technology Inc., 214 pages (2004).
Chuang et al., "Pilot Studies of Transdermal Continuous Glucose Measurement in Outpatient Diabetic Patients and in Patients during and after Cardiac Surgery," Journal of Diabetes Science and Technology, 2(4):595-602 (2008).
Exhibit B-22.pdf—Opponent's Written Response in Opposition of EP 3 730 045, Sep. 27, 2023, 43 pages.
Pickup et al., "In vivo glucose sensing for diabetes management: progress towards non-invasive monitoring," BMJ, vol. 319, 4 pages (1999).
Townsend et al., "Getting Started with Bluetooth Low Energy—Tools and Techniques for Low-Power Networking," O'Reilly Media, Inc., 180 pages (2014).
Wang et al., "A Feasible IMD Communication Protocol: Security without Obscurity," School of Engineering and Computing Sciences, NYIT Research Experience for Undergraduates (REU), May 26-Jul. 30, 2015, 1 page.
Declaration of Dr. Sayfe Kiael, Ph.D., Inter Partes Review of U.S. Pat. No. 10,375,222, 100 pages (2024).
Diallo et al., "A Secure Authentication Scheme for Bluetooth Connection," 5th International Conference on Computer & Communication Engineering, 60-63 (2014).
File History of U.S. Pat. No. 10,375,222 issued Aug. 6, 2019, Parts 1-2 (422 pages).
NFC Forum Bluetooth Special Interest Group, Bluetooth® Secure Simple Pairing Using NFC, 39 pages (2014).

Omre, "Bluetooth Low Energy: Wireless Connectivity for Medical Monitoring," Journal of Diabetes Sci Technol, vol. 4, Issue 2, 457-463, Mar. 2010.
Padgette et al., "Guide to Bluetooth Security, Recommendations of the National Institute of Standards and Technology," NET Special Publication 800421 Revision National Institute of Standards and Technology, U.S. Department of Commerce, 48 pages (2012).
Specification of the Bluetooth System Master Table of Contents & Compliance Requirements Covered Core Package version: 1.2, Current Master TOC issued: Nov. 5, 2003, 92 pages (excerpts).
Specification of the Bluetooth System Experience More Master Table of Contents & Compliance Requirements Covered Core Package version: 4.0, Current Master TOC issued: Jun. 30, 2010, 134 pages (excerpts).
Strömmer et al., "Application of Near Field Communication for Health Monitoring in Daily Life," Proceedings of the 28th IEEE FrC09., EMBS Annual International Conference, 3246-3249, Aug. 30-Sep. 3, 2006.
Townsend et al., "Getting Started with Bluetooth Low Energy," O'Reilly Media, 1-164, 180 pages (2014).
Wang et al., "A Feasible IMD Communication Protocol: Security without Obscurity," NYiT School of Engineering and Computing Sciences, 1 page (2015).
Zhang et al., "Bluetooth Low Energy for Wearable Sensor-based Healthcare Systems," 2014 Health Innovations and Point-of-Care Technologies Conference, 251-254 (2014).
Bluetooth Special Interest Group, Bluetooth® Secure Simple Pairing Using NFC, 39 pages (2014).
U.S. Pat. No. 10,375,222, issued Aug. 6, 2019, 442 pages.
Omre, "Bluetooth Low Energy: Wireless Connectivity for Medical Monitoring," Journal of Diabetes Science and Technology, vol. 4, Issue 2, 457-463 (Mar. 2010).
Padgette et al., "Guide to Bluetooth Security—Recommendations of the National Institute of Standards and Technology," National Institute of Standards and Technology, U.S. Dept. Commerce, 800-121, Rev 1, 48 pages (May 2017).
Specification of the Bluetooth System, Wireless connections made easy, Master Table of Contents & Compliance Requirements, 92 pages (Nov. 2003).
Specification of the Bluetooth System, Experience More, Master Table of Contents & Compliance Requirements, 134 pages (Jun. 2010).
Strömmer et al., "Application of Near Field Communication for Health Monitoring in Daily Life," Proceedings of the 28th IEEE, EMBS Annual International Conference New York City, USA, Aug. 30-Sep. 3, 2006, 3246-3249.
Zhang et al., "Bluetooth Low Energy for Wearable Sensor-based Healthcare Systems," 2014 Health Innovations and Point-of-Care Technologies Conferences, 4 pages (2014).
BBC News, Technology, Bluetooth rival unveiled by Nokia, 2 pgs. (Oct. 4, 2006).
Bloodborne pathogens, Occupational Safety and Health Admin., Labor, 29 CFR Ch. XVII (Jul. 1, 2003 Edition) § 1910.1030, pp. 260-273.
Bluetooth Specification V 2.1, Jul. 26, 2007, pp. 1-541.
Bluetooth Specification V 2.1, Jul. 26, 2007, pp. 542-906.
Dexcom STS 7 Plus User's Guide, 2011, 144 pgs.
Dexcom STS 7 User Guide, 2007, 74 pgs.
Diglas et al., "Reduced pain perception with Pen Mate™ an automatic needle insertion device for use with an insulin pen," Practical Diabetes Int 16(2):39-41 (1999).
Electronic Authentication Guide, 123 pgs. (Aug. 2013).
Ex. 2001—A Dictionary of Computer Science, 7th edition, definition of "authentication", 3 pgs. (2016).
Ex. 2002—Newton's Telecom Dictionary, 30th edition, definition of "authenticate", 4 pgs. (2016).
Ex. 2003—The Authoritative Dictionary of IEEE Standards Terms, $7^{th}$ edition, definition of "authentication", 3 pgs. (2000).
Expert Statement of Professor Pantelis Georgiou, Aug. 9, 2024, 52 pgs.
Freestyle Navigator User Guide, 2008, 195 pgs.
Guardian Real Time User Guide, 2006, 181 pgs.

(56) References Cited

OTHER PUBLICATIONS

Hirsch, "Realistic Expectations and Practical Use of Continuous Glucose Monitoring for the Endocrinologist," J Clin Endocrinol Metab 94:2232-2238 (2009).
Hughes, "The Business of Self-Monitoring of Blood Glucose: A Market Profile," Journal of Diabetes Science and Technology, 3(5):1219-1223 (2009).
Moore, "The Potential Use of Radio Frequency Identification Devices for Active Monitoring of Blood Glucose Levels," Journal of Diabetes Science and Technology 3(1):180-183 (2009).
UPC Annex A34-Second Expert Opinion of Dr. Michael Schoemaker, Exhibits MS-5 to MS-8, Nov. 8, 2024 (43 pgs.).
UPC Exhibit MS-5 to Second Expert Opinion of Dr. Michael Schoemaker, Nov. 8, 2024 (9 pgs.).
UPC Exhibit MS-6 to Second Expert Opinion of Dr. Michael Shoemaker, Nov. 8, 2024, Part 1 (63 pgs.).
UPC Exhibit MS-6 to Second Expert Opinion of Dr. Michael Shoemaker, Nov. 8, 2024, Part 2 (63 pgs.).
UPC Exhibit MS-7 to Second Expert Opinion of Dr. Michael Shoemaker, Nov. 8, 2024 (44 pgs.).
UPC Exhibit MS-8 to Second Expert Opinion of Dr. Michael Shoemaker, Nov. 8, 2024 (25 pgs.).
Expert Statement of Andrew Varde, Aug. 9, 2024, 87 pgs.
Expert Statement of Pantelis Georgiou, Aug. 9, 2024, 52 pgs.
Feature-by-Feature comparison of claims 1 and 5 of EP921 in relation to D2 and D3, Nov. 12, 2024, 7 pgs.

\* cited by examiner

OVER-THE-AIR PROGRAMMING OF SENSING DEVICES

PRIORITY

This application claims the benefit, under 35 U.S.C. § 119(e), of U.S. Provisional Patent Application No. 63/249,735, filed 29 Sep. 2021, and U.S. Provisional Patent Application No. 63/224,088 filed 21 Jul. 2021, both of which are incorporated herein by reference.

BACKGROUND

Field of the Disclosed Subject Matter

The disclosed subject matter relates to a system for programming and re-programming a sensor for collecting and monitoring data. The sensor can include an analyte sensor for collecting and monitoring data directly from a patient. The programming and re-programming can be performed without a direct physical connection between the sensor and another device of the system that issues programming and re-programming commands.

Description of Related Art

Certain sensing devices can wirelessly transmit data to, and receive data from, other computing devices. While some of these sensing devices are equipped with powerful processors and operate using a permanent power supply, other sensing devices are designed to operate efficiently, using little power. Moreover, low-power sensing devices can be designed to be disposable and low cost, which can involve trade-offs made during design and manufacture with respect to the complexity and computing resources included in the device. For example, one such trade-off when designing sensors, such as analyte sensors, can involve designing such devices without the capability to be updated once the devices are distributed to end users. The inability to update low-power devices can be enforced through use of memory architectures that allow limited amounts of data to be written to the memory or a limited number of writes to be performed for a region of the memory. As such, the behavior and cost of low-power devices can be fixed at the time of manufacture. However, this trade-off can reduce or eliminate the ability of the manufacturer to implement new features in devices that have been distributed to end users, correct errors in the programming of such devices, and customize or personalize the behavior of such devices.

In some cases, low-power devices, including low-power sensing devices, can be reprogrammed through direct access to the device. For example, memory architectures can provide options for rewriting to memory, such as if the hardware of the device is physically or electronically manipulated into a programming mode. Yet, reprogramming can typically involve erasing the entire programming of the low-power device, which can make modular updates difficult and can introduce memory or software errors. Furthermore, direct access to the device to perform such updates can be unavailable or inconvenient to the end user, and if available, can introduce security challenges to avoid tampering or unauthorized duplication or reverse engineering of the device software.

Accordingly, there is an opportunity for methods and systems that can be implemented by low-power, and low-cost, devices, including sensing devices, to make use of secured methods of re-programming low-power devices without requiring direct access to the device.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the drawings.

To achieve these and other advantages and in accordance with the purpose of the disclosed subject matter, as embodied and broadly described, the disclosed subject matter includes systems and methods for secured programming of sensors without direct physical connection to the sensor, such as through over-the-air (OTA) programming. The benefits and applications of the techniques described herein are not limited exclusively to medical devices, but can be implemented and used with other similar types to low-power and lost-cost devices where access to the devices once distributed to end users is inconvenient or impractical. Exemplary systems and methods can include a sensor control device that includes one or more processors, an analyte sensor, a communication module, and a memory communicatively coupled to the one or more processors, the communication module, and the analyte sensor. The memory can include storage blocks, the storage blocks including a first set of storage blocks that are in a non-programmable state and a second set of blocks that are in a programmable state. The one or more processors can receive, using the communication module, instructions to write program data to a second storage block from the second set of storage blocks that are in the programmable state, causing the second storage block to be placed into the non-programmable state and to write marking data to the memory to mark a first storage block from the first set of storage blocks that are in the non-programmable state as inaccessible. The program data written to the second storage block can include instructions that, when executed by the one or more processors, cause the one or more processors to process analyte data received from the analyte sensor. In certain embodiments, the storage blocks of the memory are dynamically-allocated memory storage blocks. In certain embodiments, the memory can be integrated with the communication module. In certain embodiments, the memory can be separate from the communication module. In certain embodiments, the memory can be a one-time programmable memory in which once data is written to the memory the data cannot be overwritten. In certain embodiments, the program data written to the second storage block can include instructions relating to features of the sensor control device, detection and calculation algorithms, or calibration data for the analyte sensor. In certain embodiments, prior to writing the marking data to the memory, the sensor control device can receive, using the communication module, a signed command. The command can be signed using an encryption key. The sensor control device can enter a programming mode. In certain embodiments, the instructions can be received as part of a communication session secured using a shared encryption key. In certain embodiments, the communication module can be compatible with a first communication protocol and the sensor control device can further include a second communication module compatible with a second communication protocol. In certain embodiments, the sensor control device can receive, using the second communication module, a command to enter a programming state prior to the one or more processors writing the marking data to the memory. In certain embodiments, one of the first communication protocol and the second communication protocol can be Bluetooth Low Energy and one of the first communication protocol and the second communication protocol can be near-field communication. In certain embodiments, the one or more processors can perform one or more integrity checks of the memory prior to executing the instructions of the program data written to the second storage block. In certain embodiments, the one or more integrity checks can include performing an integrity check on each storage block of the first set of storage blocks. In certain embodiments, the sensor control device can further include a rewritable memory communicatively coupled to the one or more processors, the communication module, and the analyte sensor. The program data written to the second storage bock can first be written to the rewriteable memory. In certain embodiments, the one or more processors can executes the instructions of program data written in storage blocks of the first set of storage blocks based on a profile stored in the rewritable memory. In certain embodiments, writing marking data to the memory to mark the first storage block as inaccessible can include modifying the profile stored in the rewritable memory. In certain embodiments, the sensor control device can, prior to the one or more processors writing marking data to the memory to mark the first storage block as inaccessible, re-initialize into an update-compatible state. In certain embodiments, the analyte sensor can be configured to generate the analyte data. The analyte data can be indicative of levels of an analyte in a fluid of a patient using the analyte sensor. Processing the analyte data received from the analyte sensor can include analyzing the analyte data using program data written to the storage blocks of the first set of storage blocks and transmitting the analyte data to an external device using the communication module. In certain embodiments, the analyte can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. In certain embodiments, the analyte data can further include temperature, heart rate, blood pressure, or movement data.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the methods and systems of the disclosed subject matter. Together with the description, the drawings explain the principles of the disclosed subject matter.

BRIEF DESCRIPTION OF THE DRAWINGS

The details of the subject matter set forth herein, both as to its structure and operation, may be apparent by study of the accompanying figures, in which like reference numerals refer to like parts.

DETAILED DESCRIPTION OF EXAMPLE EMBODIMENTS

Figure 1:
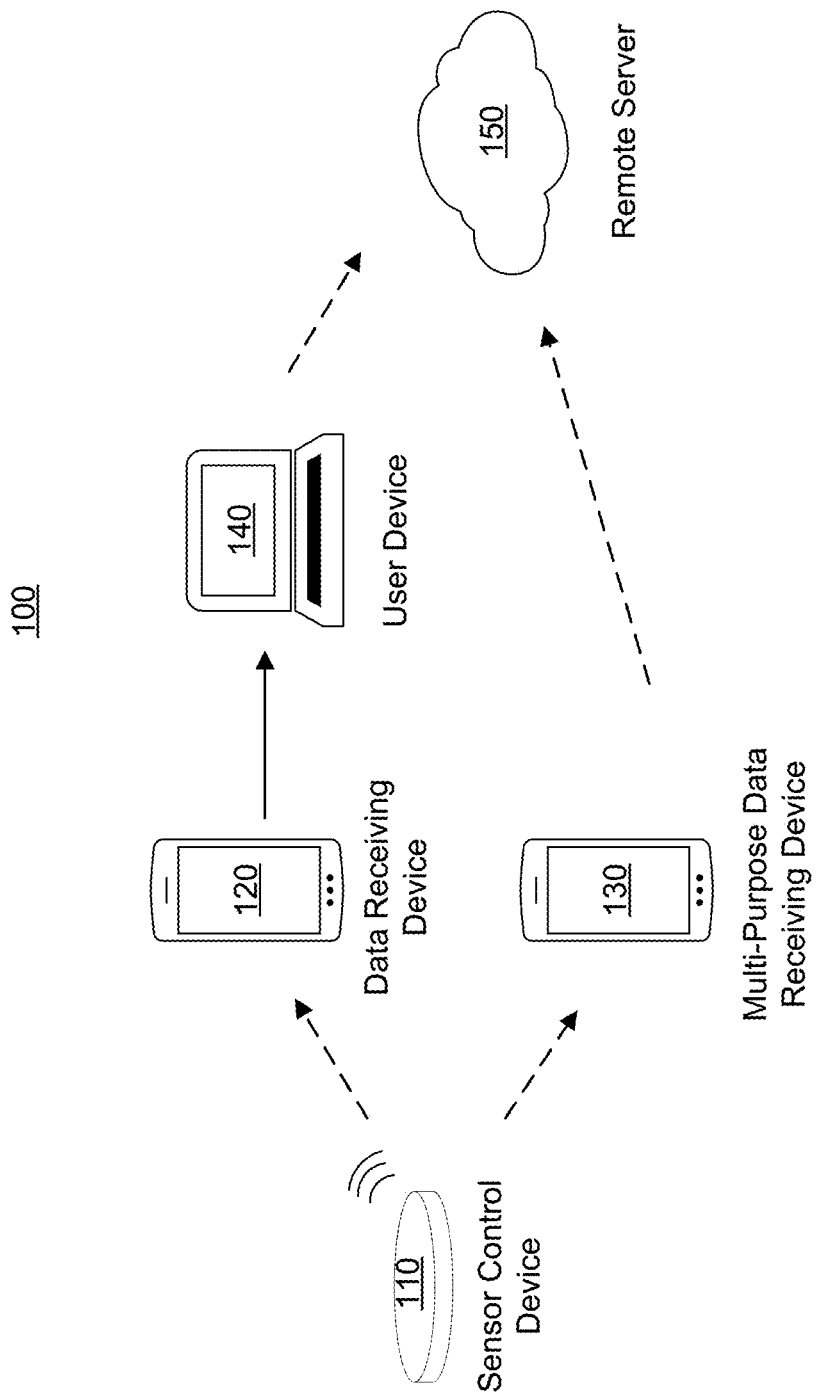
FIG. 1 is a diagram illustrating an operating environment of an example analyte monitoring system for use with the techniques described herein.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system The systems and methods presented herein can be used for secured updating of sensor control devices without direct physical access to the sensor control device. Embodiments of the disclosed subject matter include so-called over-the-air (OTA) updating. As used herein, "medical sensor" or "analyte sensor" can refer to any device capable of receiving sensor information from a user useful for medical or non-medical purposes, and can particularly refer to small-format, low-power devices, including for purpose of illustration but not limited to, body temperature sensors, blood pressure sensors, pulse or heart-rate sensors, glucose level sensors, analyte sensors, physical activity sensors, body movement sensors, or any other sensors useful for medical or non-medical monitoring purposes. Analytes measured by the analyte sensors can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. The purpose and advantages of the disclosed subject matter will be set forth and apparent from the description that follows. Additional advantages of the disclosed subject matter will be realized and attained by the methods, apparatus, and devices particularly pointed out in the written description and claims thereof, as well as from the appended drawings. Although certain embodiments are described in the context of medical devices and medical sensors, the benefits and applications of the techniques described herein are not limited exclusively to medical devices, but can be implemented and used with other similar types to low-power and lost-cost devices where access to the devices once distributed to end users is inconvenient or impractical.

For purpose of illustration and not limitation, the disclosed subject matter includes systems and methods for secured programming of medical and non-medical sensors without direct physical connection to the sensor, such as through over-the-air (OTA) programming. The benefits and applications of the techniques described herein are not limited exclusively to medical devices, but can be implemented and used with other similar types to low-power and lost-cost devices where access to the devices once distributed to end users is inconvenient or impractical. Exemplary systems and methods can include an analyte sensor or other sensor control device that includes one or more processors, an analyte sensor, a communication module, and a memory communicatively coupled to the one or more processors, the communication module, and the analyte sensor. The memory can include storage blocks, the storage blocks including a first set of storage blocks that are in a non-programmable state and a second set of blocks that are in a programmable state. The one or more processors can receive, using the communication module, instructions to write program data to a second storage block from the second set of storage blocks that are in the programmable state, causing the second storage block to be placed into the non-programmable state and to write marking data to the memory to mark a first storage block from the first set of storage blocks that are in the non-programmable state as inaccessible. The program data written to the second storage block can include instructions that, when executed by the one or more processors, cause the one or more processors to process analyte data received from the analyte sensor. In certain embodiments, the storage blocks of the memory are dynamically-allocated memory storage blocks. In certain embodiments, the memory can be integrated with the communication module. In certain embodiments, the memory can be separate from the communication module. In certain embodiments, the memory can be a one-time programmable memory in which once data is written to the memory the data cannot be overwritten. In certain embodiments, the program data written to the second storage block can include instructions relating to features of the analyte sensor or sensor control device, detection and calculation algorithms, or calibration data for the analyte sensor.

In certain embodiments, prior to writing the marking data to the memory, the analyte sensor or sensor control device can receive, using the communication module, a signed command. The command can be signed using an encryption key. The analyte sensor or sensor control device can enter a programming mode. In certain embodiments, the instructions can be received as part of a communication session secured using a shared encryption key. In certain embodiments, the communication module can be compatible with a first communication protocol and the analyte sensor or sensor control device can further include a second communication module compatible with a second communication protocol. In certain embodiments, the analyte sensor or sensor control device can receive, using the second communication module, a command to enter a programming state prior to the one or more processors writing the marking data to the memory. In certain embodiments, one of the first communication protocol and the second communication protocol can be Bluetooth Low Energy and one of the first communication protocol and the second communication protocol can be near-field communication. In certain embodiments, the one or more processors can perform one or more integrity checks of the memory prior to executing the instructions of the program data written to the second storage block. In certain embodiments, the one or more integrity checks can include performing an integrity check on each storage block of the first set of storage blocks. In certain embodiments, the analyte sensor or sensor control device can further include a rewritable memory communicatively coupled to the one or more processors, the communication module, and the analyte sensor. The program data written to the second storage bock can first be written to the rewriteable memory.

According to aspects of the disclosed subject matter, the one or more processors can executes the instructions of program data written in storage blocks of the first set of storage blocks based on a profile stored in the rewritable memory. In certain embodiments, writing marking data to the memory to mark the first storage block as inaccessible can include modifying the profile stored in the rewritable memory. In certain embodiments, the analyte sensor or sensor control device can, prior to the one or more processors writing marking data to the memory to mark the first storage block as inaccessible, re-initialize into an update-compatible state. In certain embodiments, the analyte sensor can be configured to generate the analyte data. The analyte data can be indicative of levels of an analyte in a fluid of a patient using the analyte sensor. Processing the analyte data received from the analyte sensor can include analyzing the analyte data using program data written to the storage blocks of the first set of storage blocks and transmitting the analyte data to an external device using the communication module. In certain embodiments, the analyte can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. In certain embodiments, the analyte data can further include temperature, heart rate, blood pressure, or movement data.

For purpose of illustration and not limitation, reference is made to the exemplary embodiment of an analyte monitoring system 100 for use with the disclosed subject matter as shown in FIG. 1. The analyte monitoring system 100 can be adapted to include sensors and devices for non-medical uses instead of or in addition to medical uses. FIG. 1 illustrates an operating environment of a, preferably, low-power analyte monitoring system 100 capable of embodying the techniques described herein. The analyte monitoring system 100 can include a system of components designed to provide monitoring of parameters of a human or animal body or can provide for other operations based on the configurations of the various components. For example, the analyte monitoring system 100 can provide continuous glucose monitoring to users or can provide for the delivery of drugs and other medicants. As embodied herein, the system can include a low-power sensing device 110, also referred to as a sensor worn by the user or attached to the body for which information is being collected. As embodied herein, the sensor control device 110 can be a sealed, disposable device, to improve ease of use and reduce risk of tampering, as discussed further herein. The low-power analyte monitoring system 100 can further include a reading device 120 configured as described herein to facilitate retrieval and delivery of data, including analyte data, from the sensor control device 110.

As embodied herein, the analyte monitoring system 100 can, additionally or alternatively, include a software or firmware library or application provided to a third-party and incorporated into a multi-purpose hardware device 130 such as a mobile phone, tablet, personal computing device, or other similar computing device capable of communicating with the sensor control device 110 over a communication link. Multi-purpose hardware can further include embedded devices, including, but not limited to insulin pumps or insulin pens, having an embedded library configured to communicate with the sensor control device 110. Multi-purpose device 130 embodying and executing the software library can be referred to as a data receiving device for communicating with the sensor control device 110. As used herein, a data receiving device 120 refers to a hardware device specifically manufactured for communicating with the sensor control device 110 within the analyte monitoring system 100 whereas a multi-purpose data receiving device 130 refers to a suitably configured hardware device which incorporates the software or firmware library or is executing the application. As used herein, a data communicating device refers to either or both of a data receiving device 120 or a multi-purpose data receiving device 130. It will be understood that the security architecture and design principles discussed herein are equally applicable to any suitably configured system involving a sensor control device 110, a suitably configured data receiving device 120 or multi-purpose data receiving device 130, and other similar components as those described herein. The role of the sensor control device 110 can be defined by the nature of the sensing hardware embodied in the sensor control device 110.

As embodied herein, the sensor control device 110 can include small, individually-packaged disposable devices with a predetermined active use lifetime (e.g., 1 day, 14 days, 30 days, etc.). Sensors 110 can be applied to the skin of the patient body remain adhered over the duration of the sensor lifetime. As embodied herein, sensors 110 can be designed to be selectively removed and remain functional when reapplied.

Although the illustrated embodiments of the analyte monitoring system 100 include only one of each of the sensor control device 110, data receiving device 120, multi-purpose data receiving device 130, user device 140, and remote server 150, this disclosure contemplates the analyte monitoring system 100 incorporate multiples of each components interacting throughout the system. For example, the embodiments disclosed herein include multiple sensors 110 that can be associated with multiple patients which are in communication with the remote server 150. Additionally, the remote server is illustrated as a single entity 150, however will be understood that it can encompass multiple networked servers that can be geographically distributed to reduce latency and introduce deliberate redundancy to avoid monitoring system downtime.

Figure 2:
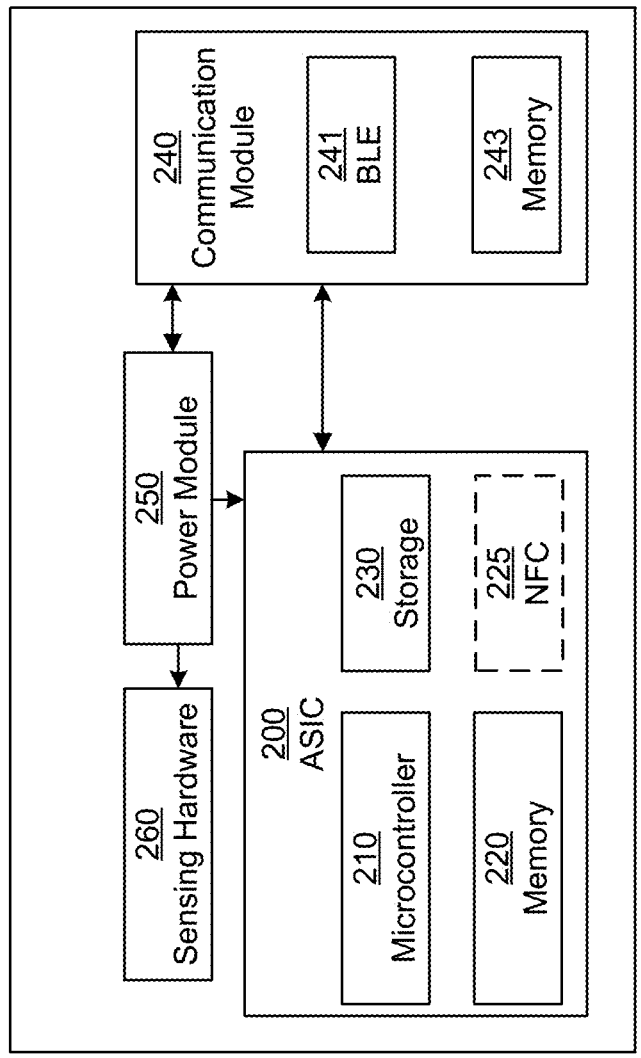
FIG. 2 is a block diagram illustrating an example sensor according to exemplary embodiments of the disclosed subject matter.

For purpose of illustration and not limitation, reference is made to the exemplary embodiment of a sensor control device 110 for use with the disclosed subject matter as shown in FIG. 2. FIG. 2 illustrates a block diagram of an example sensor control device 110 according to exemplary embodiments compatible with the security architecture and communication schemes described herein. As embodied herein, the sensor control device 110 can include an Application-Specific Integrated Circuit ("ASIC") 200 communicatively coupled with a communication module 240. As an example only and not by way of limitation, example communication modules 240 can include a Bluetooth Low-Energy ("BLE") chipset 241, Near-Field Communication ("NFC") chipset, or other chipsets for use with similar short-range communication schemes, such as a personal area network according to IEEE 802.15 protocols, IEEE 802.11 protocols, infrared communications according to the Infra-red Data Association standards (IrDA), etc. The communication module 240 can transmit and receive data and commands via interaction with similarly-capable communication modules of a data receiving device 120 or multi-purpose data receiving device 130. As embodied herein, certain communication chipsets can be embedded in the ASIC 200 (e.g., an NFC antennae 225).

As embodied herein, as the sensor control device 110 is designed to be power-efficient, low-cost, and possibly disposable, the ASIC 200 can include a microcontroller core 210, on-board memory 220, and storage memory 230. The storage memory 230 can store data used in an authentication and encryption security architecture. The data can have various elements and uses, including as described in the examples herein. The ASIC 200 can receive power from a power module 250, such as an on-board battery or from an NFC pulse. The power module 250 can store only a relatively small charge. As embodied herein, the sensor control device 110 can be a disposable device with a predetermined life span, and without wide-area network communication capability. As embodied herein, the communication module 240 can provide for communication under battery power.

Although this disclosure is described with respect to exemplary configurations of the sensor control device 110 and the ASIC 200, other suitable configurations are envisioned. As an example, processing hardware of the sensor control device 110 can be implemented as another type of special-purpose processor, such as a field programmable gate array (FPGA). As embodied herein, the processing hardware of the sensor control device 110 can include a general-purpose processing unit (e.g., a CPU) or another programmable processor that is temporarily configured by software to execute the functions of the sensor control device 110. More generally, the processing hardware can be implemented using hardware, firmware, software, or a suitable combination of hardware, firmware, and software. For purpose of illustration and not limitation, the processing hardware of the sensor control device 110 can be defined by one or more factors including computational capability, power capacity, memory capacity, availability of a network connection, etc.

As embodied herein, the communication module 240 of the sensor 100 can be or include one or more modules to support the sensor control device 110 communicating with other devices of the analyte monitoring system 100. In certain embodiments, the sensor control device 110 can communicate, for example, with a data receiving device 120 or user device 140. The communication module 240 can include, for example, a cellular radio module. The cellular radio module can include one or more radio transceivers and/or chipsets for communicating using broadband cellular networks, including, but not limited to third generation (3G), fourth generation (4G), and fifth generation (5G) networks. Using the cellular radio module the sensor control device 110 can communicate with the remote devices (e.g., remote server 150) to provide analyte data (e.g., sensor readings) and can receive updates or alerts for the user.

As another example, the communication module 240 can include a BLE module 241 and/or an NFC module to facilitate communication with a data receiving device 120 or user device 140 acting as a NFC scanner or BLE endpoint. As used throughout this disclosure, Bluetooth Low Energy ("BLE") refers to a short-range communication protocol optimized to make pairing of Bluetooth devices simple for end users. The communication module 240 can include additional or alternative chipsets for use with similar short-range communication schemes, such as a personal area network according to IEEE 802.15 protocols, IEEE 802.11 protocols, infrared communications according to the Infra-red Data Association standards (IrDA), etc. The communication module 240 can transmit and receive data and commands via interaction with similarly-capable communication modules of a data receiving device 120 or user device 140. Certain communication chipsets can be embedded in the ASIC 200 (e.g., an NFC antennae loop). Additionally, although not illustrated, the communication module 240 of the sensor control device 110 can include a radio for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)).

The communication module 243 can further include a memory 243 of its own that is coupled with a microcontroller core for the communication module 240 and/or is coupled with the microcontroller core 210 of the ASIC 200 of the sensor control device 110. In particular embodiments, and as described herein, one or more of the memory 220 of the ASIC 200 and the memory 243 of the communication module 240 can each be a so-called "one-time programmable" (OTP) memory, which can include supporting architectures or otherwise be configured to define the number times to which a particular address or region of the memory can be written, which can be one time or more than one time up to the defined number of times after which the memory can be marked as unusable or otherwise made unavailable for programming. Subject matter disclosed herein relate to systems and method for updating said OTP memories with new information. In particular, subject matter disclosed herein relate to systems and method for updating said OTP memories with information using OTA programming.

As embodied herein, the sensor control device 110 can use application layer encryption using one or more block ciphers to establish mutual authentication and encryption of other devices in the analyte monitoring system 100. The use of a non-standard encryption design implemented in the application layer has several benefits. One benefit of this approach is that in certain embodiments the user can complete the pairing of a sensor control device 110 and another device with minimal interaction, e.g., using only an NFC scan and without requiring additional input, such as entering a security pin or confirming pairing To perform analyte monitoring or medical functionalities, the sensor 100 can further include suitable sensing hardware 260 appropriate to its function. As embodied herein, the sensing hardware 260 can include, for example, medical hardware such as an autoinjector prescribed to a patient for self-administering a drug or other medicament. Accordingly, the sensing hardware 260 can include a mechanism that drives a needle or a plunger of a syringe in order to subcutaneously deliver a drug. The syringe can be pre-filled with the drug and can operate in response to a triggering event. For example, the mechanism can drive the needle into the patient and advance the plunger to deliver the drug subcutaneously via the needle.

As embodied herein, the sensing device 110 can be configured as an on-body injector attachable to a patient's body tissue (e.g., skin, organ, muscle, etc.) and capable of automatically delivering a subcutaneous injection of a fixed or patient-selected dose of a drug over a controlled or selected period of time. In such embodiments, the sensing hardware 260 or sensing device can include, for example, an adhesive or other means for temporarily attaching the sensing hardware 260 to the patient's body tissue, a primary container for storing a drug or medicament, a drive mechanism configured to drive or permit the release of a plunger to discharge the drug from the primary container, a trocar (e.g., a solid core needle), a flexible cannula disposed around the trocar, an insertion mechanism configured to insert the trocar and/or flexible cannula into the patient and optionally retract the trocar leaving the flexible cannula in the patient, a fluid pathway connector configured to establish fluid communication between the primary container and the flexible cannula upon device activation, and an actuator (e.g., a user displaceable button) configured to activate the device. As embodied herein, the on-body injector can be pre-filled and/or pre-loaded.

In addition to mechanical components, the sensing hardware 260 can include electric and/or electronic components. For example, an electronic switch can be coupled to the mechanism. The sensing device 110 can establish an authenticated communication, receive an encrypted signal, decrypt the signal using the techniques of this disclosure, determine that the signal includes a command to operate the switch, and cause the switch to drive the needle. Thus, the sensing device embodied herein can be configured to perform a function using the sensing hardware 260 in response to a remote command.

As embodied herein, the sensing hardware 260 can include a travel sensor and an analog-to-digital converter to generate a digital signal indicative of the distance travelled by the needle or plunger. Upon delivering the medicament, the low-power sensing device 110 can obtain a reading from the sensor, encrypt the reading using the techniques of this disclosure, and securely report the reading to another device. Additionally or alternatively, the sensing device 110 can report other measurements or parameters, such as a time at which the medicant was delivered, volume of medicant delivered, any issues encountered while delivering the medicament, etc. The sensing device 110 can be configured to provide data related to the operation of the sensing hardware 260 to a remote device.

The sensing hardware 260 can be configured to implement any suitable combination of one or more medical and non-medical functions and can include one or more sensing components. Sensing components can be configured to detect an operational state of the sensing device 110 (e.g., unpackaged/ready for administration, sterile barrier removal, contact with patient's body tissue, cannula and/or needle insertion, drug delivery initiation, actuator or button displacement, drug delivery completion, plunger position, fluid pathway occlusion, etc.), a condition of the sensing device 110 or of a drug contained therein (e.g., temperature, shock or vibration exposure, light exposure, drug color, drug turbidity, drug viscosity, geographic location, spatial orientation, temporal information, ambient air pressure, etc.), and/or physiological information about the patient (e.g., body temperature, blood pressure, pulse or heart rate, glucose levels, physical activity or movement, fingerprint detection, etc.). This detected information can be offloaded from the sensor control device 110 to facilitate storage and analysis, for example to a data receiving device 120, multi-purpose data receiving device 130, or remote server 150. As embodied herein, the sensor control device 110 can be configured to both receive encrypted data from other devices and transmit encrypted data to the other devices.

Referring still to FIG. 2, the ASIC 200 of the sensor control device 110 can be configured to dynamically generate authentication and encryption keys using the data retained within the storage memory 230. The storage memory 230 can also be pre-programmed with a set of valid authentication and encryption keys to use with particular classes of devices. The ASIC 200 can be further configured to perform authentication procedures with other devices (e.g., handshake, mutual authentication, etc.) using received data and apply the generated key to sensitive data prior to transmitting the sensitive data, such as sending the sensitive data to the remote server 150 via the communication module 240. The generated key can be unique to the sensor control device 110, unique to a pair of devices (e.g., unique to a particular pairing of a sensor control device 110 and a data receiving device 120), unique to a communication session between a sensor control device 110 and other device, unique to a message sent during a communication session, or unique to a block of data contained within a message. The techniques implemented by the ASIC 200 and communication module 240 of the sensor control device 110 are discussed in more detail herein.

Figure 3:
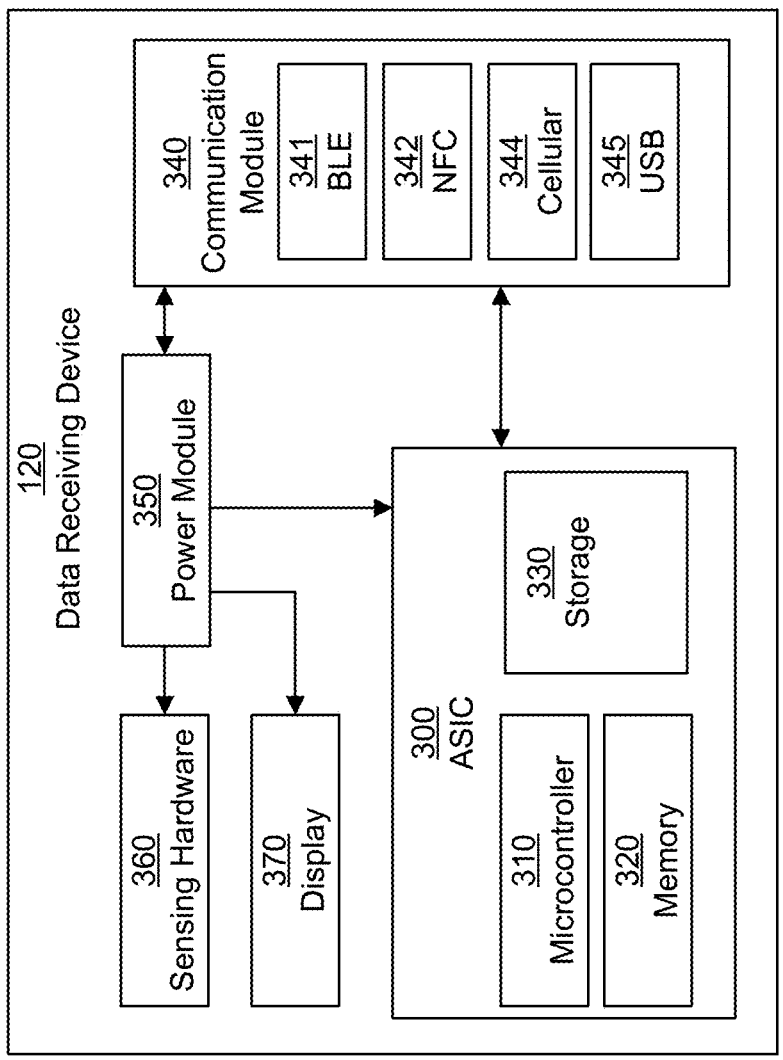
FIG. 3 is a block diagram illustrating an example data receiving device for communicating with the sensor according to exemplary embodiments of the disclosed subject matter.

For purpose of illustration and not limitation, reference is made to the exemplary embodiment of a data receiving device 120 for use with the disclosed subject matter as shown in FIG. 3. FIG. 3 illustrates an example data receiving device 120 compatible with the security and computing architecture described herein with respect to exemplary embodiments. As embodied herein, the data receiving device 120 can include a small-form factor device. The data receiving device 120 can optionally not be as memory- or processing-power constrained as the sensor control device 110, and as embodied herein, the data receiving device 120 can include sufficient memory for operational software storage and data storage, and sufficient RAM for software execution to communicate with sensor control device 110 as described herein. As illustrated in FIG. 3, the data receiving device 120 includes an ASIC 300 including a microcontroller 310, memory 320, and storage 330 and communicatively coupled with a communication module 340. As embodied herein, the ASIC 300 can be identical to the ASIC 200 of the sensor control device 110. Alternatively, the ASIC 300 can be configured to include additional computing power and functionality. Power for the components of the data receiving device 120 can be delivered by a power module 350, which as embodied herein can include a rechargeable battery, allowing for sustained operations and continued use.

The data receiving device 120 can further include a display 370 for facilitating review of analyte data received from a sensor control device 110 or other device (e.g., user device 140 or remote server 150). The display 370 can be a power-efficient display with a relatively low screen refresh rate to conserve energy use and further reduce the cost of the data receiving device 120. The display 370 can be a low-cost touch screen to receive user input through one or more user interfaces. Although not illustrated, the data receiving device 120 can include separate user interface components (e.g., physical keys, light sensors, microphones, etc.). Power for the components of the data receiving device 120 can be delivered by a power module 350, which as embodied herein can include a rechargeable battery, allowing for sustained operations and continued use.

Although illustrated as separate components, in particular embodiments, a processor of the communication module 340 can perform the processing operations ordinarily performed by the microcontroller 310 of the ASIC 300. Therefore, the ASIC 300 can be removed, and memory and other storage added to the communication module to simplify the hardware required of the data receiving device 120.

The communication module 340 can include a BLE 341 module and an NFC module 342. The data receiving device 120 can be configured to wirelessly couple with the sensor control device 110 and transmit commands and data to the sensor control device 110. As embodied herein, the data receiving device 120 can be configured to operate, with respect to the sensor control device 110 as described herein, as an NFC scanner and a BLE end point via specific modules (e.g., BLE module 342 or NFC module 343) of the communication module 340. For example, the data receiving device 120 can issue commands (e.g., OTA programming commands) to the sensor control device 110 using a first module of the communication module 340 and transmit data (e.g., OTA programming data) to the sensor control device 110 using a second module of the communication module 340.

As embodied herein, the data receiving device 120 can be configured for communication via a Universal Serial Bus (USB) module 345 of the communication module 340. The data receiving device 120 can communicate with a user device 140 for example over the USB module 345. The data receiving device 120 can, for example, receive software or firmware updates via USB, receive bulk data via USB, or upload data to the remote server 150 via the user device 140. USB connections can be authenticated on each plug event. Authentication can use, for example, a two-, three-, four-, or five-pass design with different keys. The USB system can support a variety of different sets of keys for encryption and authentication. Keys can be aligned with differential roles (clinical, manufacturer, user, etc.). Sensitive commands that can leak security information can trigger authenticated encryption using an authenticated additional keyset.

As another example, the communication module 340 can include, for example, a cellular radio module 344. The cellular radio module 344 can include one or more radio transceivers for communicating using broadband cellular networks, including, but not limited to third generation (3G), fourth generation (4G), and fifth generation (5G) networks. Using the cellular radio module 344 the data receiving device 120 can communicate with the remote server 150 to receive analyte data or provide updates or input received from a user (e.g., through one or more user interfaces). Additionally, although not illustrated, the communication module 340 of the data receiving device 120 can include a radio for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)).

As used throughout this disclosure, Bluetooth Low Energy ("BLE") refers to a short-range communication protocol optimized to make paring of Bluetooth devices simple for end users. As described herein, the use of BLE on the sensor control device 110 can optionally not rely on standard BLE implementation of Bluetooth for security but can instead use application layer encryption using one or more block ciphers to establish mutual authentication and encryption. The use of a non-standard encryption design implemented in the application layer has several benefits. One benefit of this approach is that the user can complete the pairing of the sensor control device 110 and data receiving device 120 with only an NFC scan and without involving the user providing additional input, such as entering a security pin or confirming BLE pairing between the data receiving device and the sensor control device 110. Another benefit is that this approach mitigates the potential to allow devices that are not in the immediate proximity of the sensor control device 110 to inadvertently or intentionally pair, at least in part because the information used to support the pairing process is shared via a back-up short-range communication link (e.g., NFC) over a short range instead of over the longer-range BLE channel. Furthermore, as BLE pairing and bonding schemes are not involved, pairing of the sensor control device 110 can avoid implementation issues by chip vendors or vulnerabilities in the BLE specification.

As embodied herein, the on-board storage 330 of the data receiving device 120 can be capable of storing analyte data received from the sensor control device 110 over an extended period of time. Further, the multi-purpose data receiving device 130 or a user computing device 140 as embodied herein can be configured to communicate with a remote server 150 via a wide area network. As embodied herein, the sensor control device 110 can provide sensitive data to the data receiving device 120 or multi-purpose data receiving device 130. The data receiving device 120 can transmit the sensitive data to the user computing device 140. The user computing device 140 (or the multi-purpose data receiving device 130) can in turn transmit that data to a remote server 150 for processing and analysis. In communicating with the remote server 150, multi-purpose data receiving device 130 and user computing device 140 can generate unique user tokens according to authentication credentials entered by a user and stored at the respective device. The authentication credentials can be used to establish a secure connection to the remote server 150 and can be further used to encrypt any sensitive data provided to the remote server 150 as appropriate. As embodied herein multi-purpose data receiving device 130 and user computing device 140 can optionally not be as restricted in their use of processing power, and therefore, standard data encryption and transmission techniques can be used in transmitted to the remote server 150.

As embodied herein, the data receiving device 120 can further include sensing hardware 360 similar to, or expanded from, the sensing hardware 260 of the sensor control device 110. As an example only, and not by way of limitation, in an embodiment in which the sensing hardware 260 of the sensor control device 110 is configured for continuous glucose monitoring, the sensing hardware 360 of the data receiving device 120 can be configured with a blood glucose meter, compatible for use with blood glucose test strips, thus expanding on the blood glucose monitoring of the sensor control device 110.

Figure 4:
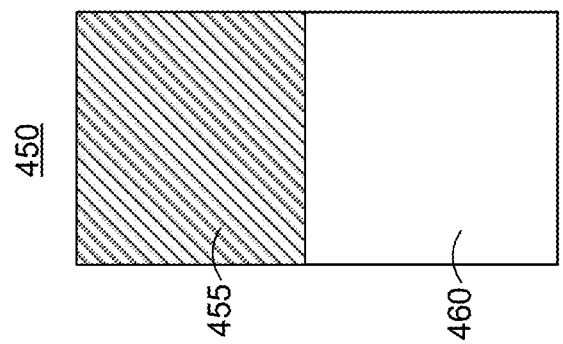
FIG. 4 is a diagram illustrating examples of organizing and allocating data in memory of a sensor according to the disclosed subject matter.
Figure 4:
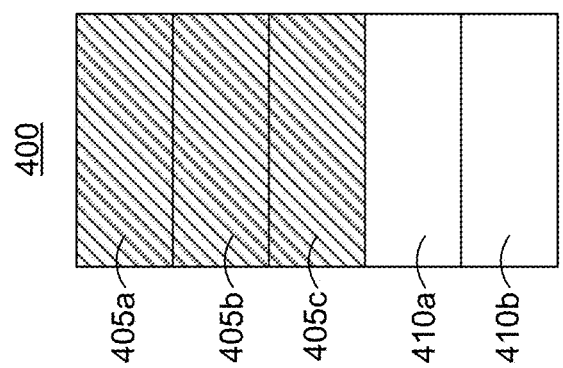

FIG. 4 illustrates exemplary embodiments for organizing data in a memory, such as the memory 220 or 243 of the sensor control device 110. In a first embodiment, the memory 400 is prearranged into multiple pre-allocated memory blocks or containers. The containers are pre-allocated into a fixed size. Containers 405a, 405b, and 405c have data written to them and, if memory 400 is one-time programming memory or a memory with otherwise-limited programming access, the containers 405a, 405b, and 405c can be considered to be in a non-programmable state. The containers 410a and 410b, though of the same size as the containers 405a, 405b, and 405c have not yet been written to. Containers 410a and 410b are thus considered to presently be in a programmable or writable state. Once containers 410a and 410b are written, they can be placed into an unprogrammable or unwritable state. The use of containers of a fixed size can be advantageous, for example to provide high portability of data blocks. By pre-allocating the size of the data blocks, memory 400 can simplify the process of replacing code blocks or supplementing with new features. Additionally, in this manner, the system can determine the number of remaining times to which the memory 400 can be added by counting the number of available containers. Containerizing the memory 400 in this fashion can improve the transportability of code and data to be written to the memory 400. Containerizing the memory 400 can also increase the resilience of the memory 400 to unintentional errors because code blocks can be written in line with the memory boundaries. As such, updating the software of a device (e.g., the sensor control device described herein) stored in memory 400 can be performed by superseding only the code in a particular previously-written container or containers with updated code written to a new container or containers, rather than replacing the entire code in the memory, as described herein. This can reduce or prevent introduction of software, firmware, or memory errors. Containerizing the memory 400 can also ensure that data or instructions written to a previously-written container or containers, such as data or instructions otherwise irrelevant to data or instructions being updated cannot be modified.

In a second embodiment, the memory 450 is not prearranged. Instead, the space allocated for data is dynamically-allocated or determined as needed. The size of programmed data can be tightly controlled, potentially increasing the usage rate of memory. The programmed segment 455 of the memory can be considered in an unprogrammable state. The segment of programmable memory 460 is unallocated and unwritten. To write data to the segment of programmable memory 460, a control unit, memory management unit, or other structure must first request a portion of unallocated memory to be allocated for writing by the control unit. The control unit can specify the size of the memory to be allocated, potentially reducing or preventing wasted space, for example, when code blocks do not line up directly with the size of containers in pre-allocated memory. Small incremental updates can be issued, as containers of varying sizes can be defined where updates are anticipated. However, care must be taken to ensure that an adequate amount of memory is available for allocation when writing to memory, such as to expand on device functions. If an update is pushed to a device (e.g., the sensor control device as described herein) is greater in size than the unallocated region 460 of the memory 450, then the update can fail or be rejected.

Figure 5:
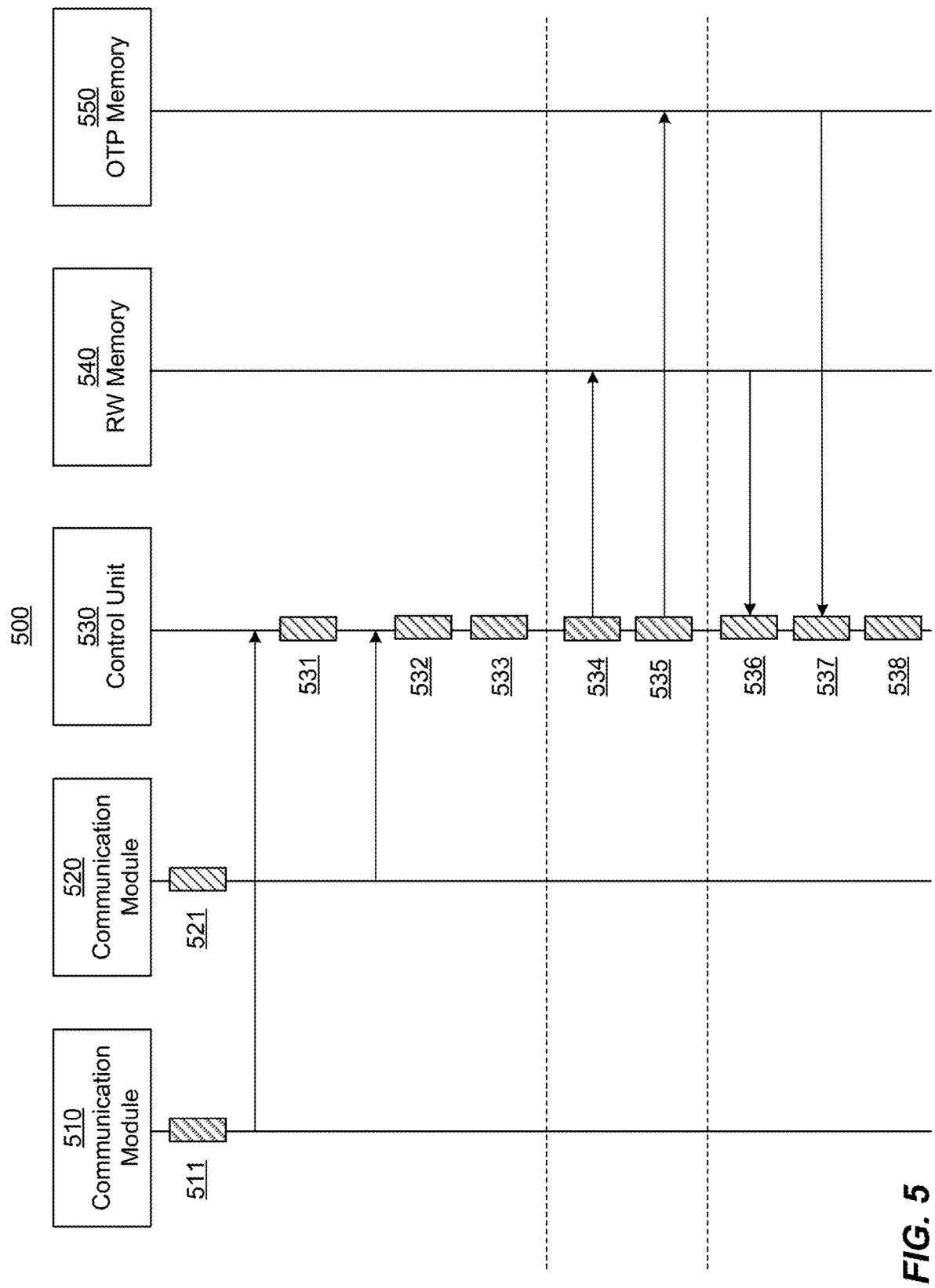
FIG. 5 is a diagram illustrating an example operational and data flow for over-the-air programming of a sensor according to the disclosed subject matter.

FIG. 5 is a diagram illustrating an example operational and data flow for over-the-air (OTA) programming of a memory in a sensor control device as well as use of the memory after the OTA programming in execution of processes by the sensor control device according to the disclosed subject matter. In the example OTA programming 500 illustrated in FIG. 5, a request is sent from an external device (e.g., the data receiving device 130) to initiate OTA programming (or re-programming). At 511, one or more of the communication modules 510 of a sensor control device (e.g., sensor control device 110) receives an OTA programming command. The communication module 510 sends the OTA programming command to the control unit 530 of the sensor control device (e.g., a microcontroller 210 of an ASIC 200).

With continued reference to FIG. 5, at 531, after receiving the OTA programming command, the control unit 530 validates the OTA programming command. The control unit 530 can determine, for example, whether the OTA programming command is signed with a digital signature token associated with a manufacturer of the sensor control device or an authorized representative thereof. Upon determining that the OTA programming command is valid, the control unit 530 can set the sensor control device into an OTA programming mode.

At 521, a second one or more of the communication modules 520 receives data to be used for reprogramming the sensor control device from an external device. The data can be received from the same external device that sent the OTA programming command but can additionally or alternatively be received from a different external device. The second communication module 520 sends the OTA programming data to the control unit 530.

Referring still to FIG. 5, at 532, the control unit 530 can validate the OTA programming data as well. Validating the OTA programming data can include determining whether the OTA programming data is signed with a digital signature token associated with the manufacturer of the sensor control device or the authorized representative thereof. In some embodiments, the digital signature token used to validate the OTA programming data can be the same digital signature token used to validate the OTA programming command. In some embodiments, different digital signature tokens can be used, for example, to further increase the security of the OTA programming procedure by using two digital signatures to protect the device. Additionally or alternatively, the OTA programming data can be encrypted using an encryption token and scheme that has been pre-assigned and/or mutually agreed upon between the sensor control device and the external device.

At 533, after validating the OTA programming data, the control unit 530 can reset the sensor control device to re-initialize the sensor control device in a programming state. Resetting and re-initializing the sensor control device can reduce the occurrence of certain automatically programmed events that, for example and without limitation, can prevent or inhibit unauthorized identification and manipulation of the programming of the sensor control device. As an example, the sensor control device can regularly halt or prevent the execution of certain commands while data is being retrieved from or communicated to the sensor control device. As another example, the sensor control device can, for example and without limitation, enforce a communication session timeout, such that communication sessions lasting longer than a threshold amount, which can be longer than an expected length of a normal communication session or burst, can be terminated as likely to be encountering an error. When data is being provided for OTA programming, an operational or communication timeout can interrupt the writing of programming data, which can render the sensor control device inoperable or cause a malfunction. After completion, the sensor control device has transitioned into an OTA programming state.

FIG. 5 illustrates one example of OTA programming 500 in which the OTA programming command and OTA programming data are received by the one or more communication modules 510 and the second one or more communication modules 520 and are subsequently relayed to the control unit 530. Additionally or alternatively, as embodied herein, the communication module 520 can be configured to wait to send the OTA programming data to the control unit 530 until after the control unit 530 has completed validation of the OTA programming command. As another example, in certain embodiments, the OTA programming data and OTA programming command can both be received by the same communication module 510. The sensor control device can include a single communication module 510, or if equipped with more than one communication module 510, can be configured to only accept OTA programming commands or OTA programming data from a single one or certain ones of the communication modules 510. As described herein, the first communication module can be configured to receive the OTA programming command from an external device, and for example and without limitation, and as embodied herein, the first communication module can include an NFC receiver or transceiver. Additionally or alternatively, and as embodied herein, the first communication module can include a receiver or transceiver compatible with a Bluetooth protocol, which can be a BLE protocol. In particular embodiments, as described herein, the first one or more communication modules 510 can be compatible with a first communication protocol, while the second one or more communication modules 520 can be compatible with a second communication protocol. For example, when the first communication module includes an NFC receiver or transceiver, the second communication module can include a receiver or transceiver compatible with a Bluetooth or BLE protocol. Similarly, when the first communication module includes a receiver or transceiver compatible with a Bluetooth or BLE protocol, the second communication module can include an NFC receiver or transceiver.

Once the sensor control device has transitioned into the OTA programming state, the control unit 530 can begin to write data to the rewriteable memory 540 of the sensor control device at 534 and write data to the OTP memory 550 of the sensor control device at 535. As described herein, the term OTP memory can refer to memory that includes access restrictions and security to facilitate writing to particular addresses or segments in the memory a predetermined number of times. As described herein, the OTP memory can be configured as a so-called "one-time programmable memory," which can be programmable one time or more than one time up to a defined number of times. Additionally or alternatively, other embodiments of memory providing for predefined instances of reprogramming are envisioned. The data written by the control unit 530 can be based on the validated OTA programming data. For example, the control unit 530 can also write data to a free or unused portion of the OTP memory 550. The control unit 530 can write data to cause one or more programming blocks or regions of the OTP memory 550 to be marked invalid or inaccessible. The data written to the free or unused portion of the OTP memory can be used to replace invalidated or inaccessible programming blocks of the OTP memory 550.

In certain embodiments, the rewriteable memory 540 of the sensor control device can include a programming manifest or profile for the software of the sensor control device. The programming manifest or profile can include a listing of the blocks of or written to the OTP memory 550. The listing can include an indication of which blocks are valid and which blocks are invalid or inaccessible. Therefore, when executing code based on the OTP memory 550, the control unit 530 can reference the listing of the blocks to determine which blocks are to be avoided. In certain embodiments, the programming manifest or profile can additionally or alternatively indicate which programming block of the OTP memory 550 follows each programming block. Then, when executing code based on the programming blocks of the OTP, the control unit 530 can use the programming manifest or profile to determine which block is to be used after a particular block or region, effectively skipping the invalidated blocks. In certain embodiments, the programming manifest or profile can additionally or alternatively identify programming blocks that have been invalidated and further identify which programming blocks have been designated as the replacement for the programming blocks. Such identification can be done by reference, so that, for example, if a valid programming block references an invalid programming block, or code stored therein, the control unit 530 can, by referencing the programming manifest or profile, determine that the valid programming block includes out-of-date references and instead retrieve the replacement programming block (or code stored therein). An illustrated example of invalidating and substituting a memory block consistent with the disclosed subject matter is provided in FIG. 6 below. Identifying which programming blocks have superseded or replaced a previously-written programming block that has been invalidated, such as by reference, facilitates the execution of software instructions included in both new and pre-existing programming blocks. When preparing the software instructions, a reference-based approach can ensure that references or calls made to other programming blocks are resolved at the appropriate, new, programming blocks without updating every instance of the location of the now-invalided programming block.

After the control unit 530 writes the data to the respective memories at 534 and 535, the control unit 530 can perform one or more software integrity checks to ensure that errors were not introduced into the programming blocks during the writing process. For example, integrity checks can be performed on individual blocks of memory, such as on the newly written blocks of memory, on the memory as a whole (or a defied region of the memory encompassing multiple programming blocks", or on a standard programming flow of the sensor control device (which can be defined in the programming manifest or profile). For example, the programming manifest can define a number of basic unit tests to perform with the newly written data that specify actions to attempt and results to anticipate. In certain embodiments, the OTA programming data received at 532 can include an integrity check value associated with the OTA programming data, such as an integrity bit or checksum value (as described herein). After writing the data to the OTP memory 550 at 535, the control unit 530 can calculate an integrity bit value or checksum value for one or more memory blocks and compare the calculated value to the value provided with the OTA programming data. If the values correspond, then the control unit 530 can continue processing. If the values differ, then the control unit 530 can take one or more remedial actions, which can include, by way of example, attempting to rewrite the data (and invalidating the memory blocks that are believed to include errors, alerting a user that an error has occurred, or alerting an external device that an error has occurred during rewriting using one of the communication modules 510 and 520. Once the control unit 530 is able to determine that the data has been written without errors, the control unit 530 can resume standard operations of the sensor control device. For example, and as embodied herein, the control unit 530 can reset the sensor control device to cause the sensor control device to re-initialize in a standard execution mode (e.g., distinct from the programming mode).

In execution mode, at 536, the control unit 530 can retrieve the programming manifest or profile from the rewriteable memory 540. As described herein, the programming manifest or profile can include a listing of the valid software programming blocks (or memory blocks generally) and can include a guide to program execution for the sensor control device. By following the programming manifest or profile, the control unit 530 can determine which memory blocks of the OTP memory 550 are appropriate to execute based on the current version of the software and avoid execution of out-of-date or invalidated programming blocks or reference to out-of-date data stored in invalidated programming blocks. At 537, according to the guide provided in the programming manifest, the control unit 530 can selectively retrieve memory blocks from the OTP memory 550. At 538, the control unit 530 can use the retrieved memory blocks, such as by executing programming code stored in the memory or using variables such as calibration parameters stored in the memory during execution. The programming code stored in the memory can include new operations or functions for the sensor control device and its components that were defined by the OTA programming data and written to memory blocks of the OTP memory. Executing the code can include using revised or updated algorithms associated with the analyte sensor or other sensing hardware (e.g., medical hardware) of the sensor control device. The revised or updated algorithms can also affect the general operation of the sensor control device, such as power-level regulation techniques or control software for a communication module. Executing the retrieved memory blocks can cause the sensor control device to collect analyte data from a patient using sensing hardware such as an analyte sensor of the sensor control device, analyze or otherwise processing the analyte data, and export, offload, or transmit the analyte data to an external device. In particular embodiments, the analyte can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. In particular embodiments the analyte data can also include other information about the patient, such as temperature, heart rate, blood pressure, or movement data.

Prior to executing the code retrieved from the OTP memory 550 at 538, the control unit 530 can perform one or more integrity checks on the retrieved memory blocks. Similar to the integrity checks performed after writing the memory blocks while in the programming mode, the control unit 530 can perform integrity checks on, for example, individual blocks of memory, the programming flow defined in the programming manifest or profile, or the entire OTP memory 550. In particular embodiments, similar integrity checks can be performed on the rewriteable memory and the corresponding memory blocks. The integrity checks can be performed, for example, during a sensor control device initialization sequence, where the control unit 530 can refuse to enter a standard operating mode if errors are detected. The integrity checks can be performed, for example, the first time that a memory block is retrieved from the rewriteable memory 540 or OTP memory 550. The integrity checks can be performed, for example, prior to execution of the instructions in the memory blocks, which can occur only selected times, such as a first time the instructions are executed, or can occur each time the memory blocks are retrieved or the corresponding instructions are executed. The timing and repetitiveness of the integrity checks can be defined for the control unit 530, e.g., in the programming manifest or profile. The timing and repetitiveness of the integrity checks can be set in according with principles of balancing sensor control device power consumption (and, therefore, sensor control device battery term and overall service term) with security of the software used to collect, monitor, and export sensitive analyte data.

Figure 6:
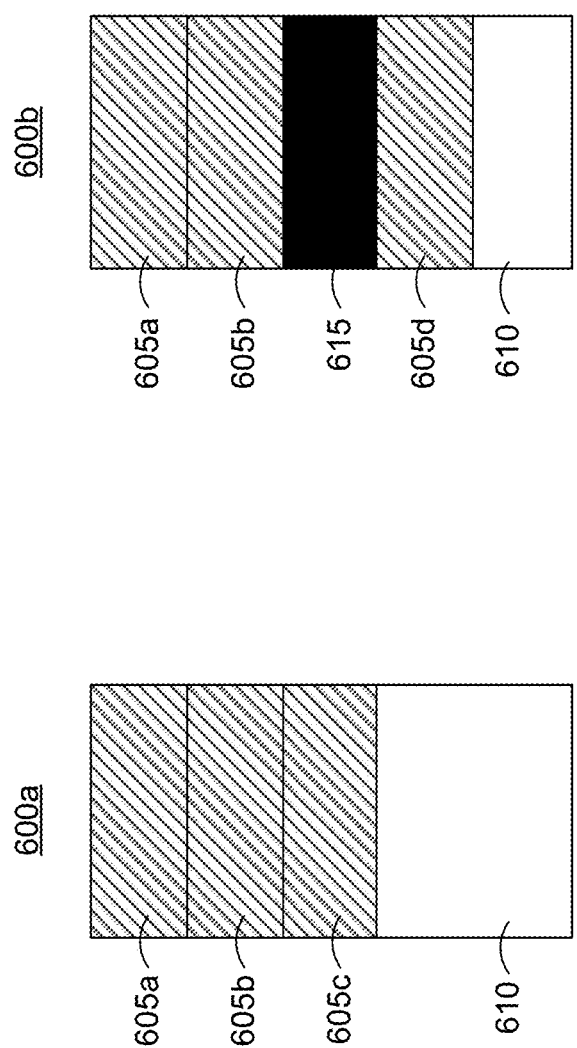
FIG. 6 is a diagram illustrating an exemplary demonstration of memory block management according to the subject matter of this disclosure.

FIG. 6 illustrates an exemplary demonstration of memory block management according to the subject matter of this disclosure. In particular, FIG. 6 illustrates an example of OTA programming according to the subject matter of this disclosure. FIG. 6 illustrates a first depiction of a memory 600a, such as a one-time programmable memory or a memory with otherwise-limited programming access. The memory includes three memory blocks or containers 605a, 605b, and 605c. As embodied herein, containers 605a, 605b, and 605c all have data written to them, and as such are in an unwritable or unprogrammable state. Such data can include, for example, operational code for execution by a control unit or variables for use during execution. The memory 600a further includes an unallocated region or segment 610. Because the segment 610 of the memory 600a is unallocated, the segment 610 is considered to be programmable memory. A control unit, memory management unit, or other similar structure can issue commands to allocate and write to a portion of the segment of programmable memory, causing the portion of the segment of programmable memory to be placed into a non-programmable state. FIG. 6 further illustrates a second depiction of a memory 600*b* after the portion 605*d* of the segment of programmable memory has been placed into a non-programmable state. Additionally, a container 615 has been marked invalid or inaccessible, indicating that that container or block of memory can be used by a control unit during execution.

Not illustrated is the manufacture of the devices used in the analyte monitoring system 100 illustrated in FIG. 1, including the sensor control device 110, data receiving device 120, as well as software or application programming interfaces that can be used by or with the remote server 150, multi-purpose data receiving devices 130, and other user devices 140. The manufacturer can choose to provide the information and programming necessary for the devices to securely communicate through secured programming and updates (e.g., one-time programming, encrypted software or firmware updates, etc.). For example, the manufacturer can provide information that can be used to generate encryption keys for each device, including secured root keys for the sensor control device 110 and optionally for the data receiving device 120 that can be used in combination with device-specific information and operational data (e.g., entropy-based random values) to generate encryption values unique to the device, session, or data transmission as need. These encryption keys can be used, for example, to validate OTA programming commands and OTA programming data transmitted from external devices (e.g., data receiving devices 120, multi-purpose data receiving devices 130, user device 140, etc.) to sensor control devices 110.

The manufacturer can imbue each sensor control device 110 with a unique identifier ("UID") and other identifying information, such as an identifier for the manufacturer, identifier for the communication module and manufacturer, or any other suitable identifying information for the sensor or sensor components. As an example, the UID can be derived from sensor-unique data, such as from a serial number assigned to each ASIC 200 embodied in the sensor control device 110 by the ASIC vendor, from a serial number assigned to a communication module 240 embodied in the sensor control device 110 by a communication module vendor, from a random value generated by the sensor manufacturer, etc. Additionally or alternatively, the UID can also be derived from manufacturing values including a lot number for the sensor control device 110 or its components, a day, date, or time of manufacturer of the sensor control device 110 or its key components, the manufacturing location, process, or line of the sensor or its key components, and other information that can be used to identify when and how the sensor was manufactured. The UID can be accompanied by encryption keys and several generated random values that are also unique to each sensor control device 110. Similar processes can be used to establish the secure identity of the data receiving device 120.

As the data collected by the sensor control device 110 and exchanged between the sensor control device 110 and other devices in the analyte monitoring system 100 pertain to information about a user, the data is highly sensitive and can be beneficial to be protected. Analyte data associated with a patient is sensitive data at least in part because this information can be used for a variety of purposes, including for health monitoring and medication dosing decisions. In addition to patient data, the analyte monitoring system 100 can enforce security hardening against efforts by outside parties to reverse-engineering. The security architecture described herein can include various combinations of control features described herein, including, but not limited to the protection of communication between devices, the protection of proprietary information within components and applications, and the protection of secrets and primary keying material. As embodied herein, encryption and authentication can be used as exemplary technical controls for providing protective features. As embodied herein, the various components of the analyte monitoring system 100 can be configured compliant with a security interface designed to protect the Confidentiality, Integrity and Availability ("CIA") of this communication and associated data. To address these CIA concerns, security functions can be incorporated into the design of the hardware and software of the analyte monitoring system 100.

As embodied herein, to facilitate the confidentiality of data, communication connections between any two devices (e.g., a sensor control device 110 and data receiving device 120) can be mutually authenticated prior to transmitting sensitive data by either device. Communication connections can be encrypted using a device-unique or session-unique encryption key. As embodied herein, the encryption parameters can be configured to change with every data block of the communication.

As embodied herein, to protect the integrity of data, encrypted communications between any two devices (e.g., a sensor control device 110 and data received device 120) can be verified with transmission integrity checks built into the communications. As an example, as described herein, OTA programming data can be verified or validated with transmission integrity checks. Furthermore, data written to a memory of the sensor control device 110 can be verified or validated with integrity checks prior to execution. As embodied herein, session key information, which can be used to encrypt the communication, can be exchanged between two devices after the devices have each been authenticated. Integrity checks can include, for example, an error detection code or error correction code, including as an example and not by way of limitation, non-secure error-detecting codes, minimum distance coding, repetition codes, parity bits, checksums, cyclic redundancy checks, cryptographic hash functions, error correction codes, and other suitable methods for detecting the presence of an error in a digital message.

As embodied herein, minimum distance coding includes a random-error correcting code that provides a strict guarantee on number of detectable errors. Minimum distance coding involves choosing a codeword to represent a received value that minimizes the Hamming distance between the value and the representation. Minimum distance coding, or nearest neighbor coding, can be assisted using a standard array. Minimum distance coding is considered useful where the probability that an error occurs is independent of the position of a given symbol and errors can be considered independent events. These assumptions can be particularly applicable for transmissions over a binary symmetric channel.

Additionally or alternatively, as embodied herein, a repetition code relates to a coding scheme that repeats bits across a channel to guarantee that communication messages are received error-free. Given a stream of data to be transmitted, the data divided into blocks of bits. Each block is transmitted and re-transmitted some predetermined number of times. An error is detected if any transmission of the repeated block differs.

In addition, or as a further alternative, as embodied herein, a checksum is a value relative to a message or stored block of data based on a modular arithmetic sum of message code words of a fixed word length. The checksum can be directed from the entire block of data or subset thereof. Checksums are generated using a checksum function or cryptographic hash function that is configured to output significantly different checksum values (or hash values) for minor changes to the targeted message. A parity bit is a bit added to a group of bits in transmission to ensure that the counted number of certain bits in the outcome is even or odd. For example, the parity bit can be used to ensure that the number of bits with value 0 is odd. A parity bit can then detect single errors or a repeating fixed number of errors. A parity bit can be considered a special case of a checksum.

As embodied herein, to further reduce or prevent unauthorized access to the devices of the analyte monitoring system 100, root keys (e.g., keys used to generate device-unique or session-unique keys) can optionally not be stored on the sensor control device 110 and can be encrypted in a storage by the remote server 150 or on other device having more computing power than the sensor control device 110 (e.g., data receiving device 120). As embodied herein, the root keys can be stored in an obfuscated manner to prevent a third-party from easily accessing the root keys. The root keys can also be stored in different states of encryption based on where in the storage they are stored. As embodied herein, to facilitate the availability of data, sensor control device 110 operations can be protected from tampering during service life, in which the sensor control device 110 can be configured to be disposable, for example and as embodied herein by restricting access to write functions to the memory 220 via a communication interface (e.g., BLE and NFC). The sensor can be configured to grant access only to known devices (e.g., identifier by a MAC address or UID) or only to devices that can provide a predetermined code associated with the manufacturer or an otherwise authenticated user. Access to read functions of the memory 220 can also be enforced, including for example where the read function attempts to access particular areas of the memory 220 that have been designated secure or sensitive. The sensor control device 110 can further reject any communication connection request that does not complete authentication within a specified amount of time to safeguard against specific denial of service attacks on the communication interface including attempted man-in-the-middle (MITM) style attacks. Furthermore, the general authentication and encryption design, described herein, can support interoperable usage where sensor control device 110 data can be made available to other "trusted" data receiving devices without being permanently bound to a single device.

As embodied herein, the devices, including sensor control device 110 and data receiving device 120, can each employ a variety of security practices to ensure the confidentiality of data exchanged over communication sessions and facilitate the relevant devices to find and establish connections with trusted endpoints. As an example, the sensor control device 110 can be configured to proactively identify and connect with trusted local-area, wide-area, or cellular broadband networks and continuously verify the integrity of those connections. The sensor control device 110 can further deny and shut down connection requests if the requestor cannot complete a proprietary login procedure over a communication interface within a predetermined period of time (e.g., within four seconds). For example and without limitation, such configurations can further safeguard against denial of service attacks.

As embodied herein, the sensor control device 110 and data receiving device 120 can support establishing long-term connection pairs by storing encryption and authentication keys associated with other devices. For example, the sensor control device 110 or data receiving device can associate a connection identifier with encryption and authentication keys used to establish a connection to another device. In this manner, the devices can re-establish dropped connections more quickly, at least in part because the devices can avoid establishing a new authentication pairing and can proceed directly to exchanging information via encrypted communication protocols. After a connection is successfully established, the device can refrain from broadcasting connection identifiers and other information to establish a new connection and can communicate using an agreed channel-hopping scheme to reduce the opportunity for third-parties to listen to the communication.

Data transmission and storage integrity can be actively managed using on-chip hardware functions. While encryption can provide a secure means of transmitting data in a tamper-proof manner, encryption and decryption can be computationally expensive processes. Furthermore, transmission failures can be difficult to differentiate from attacks. As described previously, a fast, hardware-based error detection code can be used for data integrity. As an example, as embodied herein, an appropriately-sized error detection code for the length of the message (e.g., a 16-bit CRC) can be used, although other suitable hardware-based error detection codes can be used in accordance with the disclosed subject matter. Programming instructions that access, generate, or manipulate sensitive data can be stored in memory blocks or containers that are further protected with additional security measures, for example encryption.

As embodied herein, the analyte monitoring system 100 can employ periodic key rotation to further reduce the likelihood of key compromise and exploitation. A key rotation strategy employed by the analyte monitoring system 100 can be designed to ensure backward compatibility of field-deployed or distributed devices. As an example, the analyte monitoring system 100 can employ keys for downstream devices (e.g., devices that are in the field or cannot be feasibly provided updates) that are designed to be compatible with multiple generations of keys used by upstream devices. Additionally, and according to the subject matter herein, keys can be securely updated by invalidating memory blocks including out-of-date keys which are then replaced with data written to new memory. Rotation of keys can be initiated by the manufacturer or the operator of the analyte monitoring system 100. For example, the manufacturer or operator of the analyte monitoring system 100, can generate a new set of keys or define a new set of procedures for generating keys. During manufacture of sensors 110 that are intended to use the new set of keys, the manufacturer can propagate the new set of keys to newly manufactured sensors 110. The manufacturer can also push updates to deployed devices in communication with the remote server 150 to extend the new set of keys or set of procedures for generating keys to the deployed devices. As a further alternative, key rotation can be based on an agreed-upon schedule, where the devices are configured to adjust the keys used according to some time- or event-driven function.

In addition to the specific embodiments claimed below, the disclosed subject matter is also directed to other embodiments having any other possible combination of the dependent features claimed below and those disclosed above and in the attached figures. As such, the particular features disclosed herein can be combined with each other in other manners within the scope of the disclosed subject matter such that the disclosed subject matter can be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

Embodiments disclosed herein include:

Embodiment A. A sensor control device that includes one or more processors, an analyte sensor, a communication module, and one or more memories communicatively coupled to the one or more processors, the communication module, and the analyte sensor, wherein: the one or more memories comprise a plurality of storage blocks, the plurality of storage blocks including a first set of storage blocks that are in a non-programmable state and a second set of blocks that are in a programmable state; and wherein the one or more processors are configured to receive, using the communication module, instructions to write program data to a second storage block from the second set of storage blocks that are in the programmable state, causing the second storage block to be placed into the non-programmable state and to write marking data to the memory to mark a first storage block from the first set of storage blocks that are in the non-programmable state as inaccessible; and wherein the program data written to the second storage block comprises instructions that, when executed by the one or more processors, cause the one or more processors to process analyte data received from the analyte sensor.

Embodiment A may have one or more of the following additional elements in any combination: Element 1: wherein the plurality of storage blocks of the memory are dynamically-allocated memory storage blocks; Element 2: wherein the memory is integrated with the communication module; Element 3: wherein the memory is separate from the communication module; Element 4: wherein the memory is a one-time programmable memory in which once data is written to the memory the data cannot be overwritten; Element 5: wherein the program data written to the second storage block further comprises instructions relating to features of the sensor control device, detection and calculation algorithms, or calibration data for the analyte sensor; Element 6: wherein, prior to writing the marking data to the memory, the sensor control device: receives using the communication module, a signed command, wherein the command is signed using an encryption key; and enters a programming mode; Element 7: wherein the instructions are received as part of a communication session secured using a shared encryption key; Element 8: wherein the communication module is compatible with a first communication protocol and the sensor control device further comprises a second communication module compatible with a second communication protocol; Element 9: wherein the sensor control device receives a command to enter a programming state via the second communication module prior to the one or more processors writing the marking data to the memory; Element 10: wherein one of the first communication protocol and the second communication protocol is Bluetooth Low Energy and one of the first communication protocol and the second communication protocol is near-field communication; Element 11: wherein the one or more processors are further configured to, perform one or more integrity checks of the memory prior to executing the instructions of the program data written to the second storage block; Element 12: wherein the one or more integrity checks comprise performing an integrity check on each storage block of the first set of storage blocks; Element 13: further comprising a rewriteable memory communicatively coupled to the one or more processors, the communication module, and the analyte sensor, wherein the program data written to the second storage block are first written to the rewriteable memory; Element 14: wherein the one or more processors execute the instructions of the program data written in storage blocks of the first set of storage blocks based on a profile stored in the rewriteable memory; Element 15: wherein writing marking data to the memory to mark the first storage block as inaccessible comprises modifying the profile stored in the rewriteable memory; Element 16: wherein the sensor control device is configured to, prior to the one or more processors writing marking data to the memory to mark the first storage block as inaccessible, re-initialize into an update-compatible state; Element 17: wherein the analyte sensor is configured to generate the analyte data, wherein the analyte data is indicative of levels of an analyte in a fluid of a patient using the analyte sensor; and processing the analyte data received from the analyte sensor comprises: analyzing the analyte data using the program data written to the storage blocks of the first set of storage blocks; and transmitting the analyte data to an external device using the communication module.

Embodiment B. A method comprising: receiving, by one or more processors of a sensor control device using a communication module of the sensor control device communicatively coupled with the one or more processors, instructions to write marking data to a memory of the sensor control device communicatively coupled with the one or more processors, the communication module, and an analyte sensor of the sensor control device, wherein the memory comprises a plurality of storage blocks, the plurality of storage blocks including a first set of storage blocks that are in a non-programmable state and a second set of blocks that are in a programmable state; writing, by the one or more processors, program data to a second storage block from the second set of storage blocks that are in the programmable state, causing the second storage block to be placed into the non-programmable state; writing, by the one or more processors, marking data to the memory to mark a first storage block from the first set of storage blocks that are in the non-programmable state as inaccessible; and processing, by the one or more processors, analyte data received from the analyte sensor based on executing instructions stored in the program data written to the second storage block.

Embodiment C. A computer-readable non-transitory storage media comprising instructions that are configured, when executed by one or more processors of a sensor control device, to perform operations comprising: receiving, by the one or more processors using a communication module of the sensor control device communicatively coupled with the one or more processors, instructions to write marking data to a memory of the sensor control device communicatively coupled with the one or more processors, the communication module, and an analyte sensor of the sensor control device, wherein the memory comprises a plurality of storage blocks, the plurality of storage blocks including a first set of storage blocks that are in a non-programmable state and a second set of blocks that are in a programmable state; writing, by the one or more processors, program data to a second storage block from the second set of storage blocks that are in the programmable state, causing the second storage block to be placed into the non-programmable state; writing, by the one or more processors, marking data to the memory to mark a first storage block from the first set of storage blocks that are in the non-programmable state as inaccessible; and processing, by the one or more processors, analyte data received from the analyte sensor based on executing instructions stored in the program data written to the second storage block.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A sensor control device comprising:
   one or more processors,
   a glucose sensor,
   a first communication module and a second communication module, wherein the first communication module is compatible with a first communication protocol and the second communication module is compatible with a second communication protocol, and
   one or more memories communicatively coupled to the one or more processors, the communication module, and the glucose sensor, wherein:
      a memory of the one or more memories comprises a plurality of storage blocks, wherein the memory is a one-time programmable memory and the plurality of storage blocks includes a first set of storage blocks that have been written into and are in a non-programmable state and a second set of storage blocks that have not been written into and are in a programmable state;
      the one or more processors are configured to:
         receive, using the first communication module and the first communication protocol, first instructions that instruct the one or more processors to enter into a programming mode to write program data to a second storage block of the second set of storage blocks, wherein the first instructions are signed with a first digital signature token generated based on information associated with a manufacturer of the sensor control device;
         validate the first instructions based on the first digital signature token generated based on information associated with the manufacturer of the sensor control device;
         subsequent to validating the first instructions based on the first digital signature token, enter into the programming mode;
         receive, using the second communication module and the second communication protocol, the program data, wherein the program data comprises second instructions configured for processing data received from the glucose sensor, wherein the program data is signed with a second digital signature token generated based on information associated with the manufacturer of the sensor control device;
         validate the program data based on the second digital signature token generated based on information associated with the manufacturer of the sensor control device, wherein the first digital signature token is different from the second digital signature token; and
         subsequent to validating the program data based on the second digital signature token, cause the program data to be written into the second storage block of the second set of storage blocks, cause the second storage block to be placed into the non-programmable state, and cause a first storage block of the first set of storage blocks to be marked as inaccessible.

2. The sensor control device of claim 1, wherein the plurality of storage blocks of the memory are dynamically-allocated memory storage blocks.

3. The sensor control device of claim 1, wherein the memory is integrated with the communication module.

4. The sensor control device of claim 1, wherein the memory is separate from the communication module.

5. The sensor control device of claim 1, wherein the one-time programmable memory is a memory in which data written into the memory cannot be overwritten.

6. The sensor control device of claim 1, wherein the program data written to the second storage block further comprises third instructions relating to features of the sensor control device, detection and calculation algorithms, or calibration data for the glucose sensor.

7. The sensor control device of claim 1, wherein, prior to writing the marking data to the memory, the sensor control device enters the programming mode.

8. The sensor control device of claim 1, wherein the first instructions are received as part of a communication session secured using a shared encryption key.

9. The sensor control device of claim 1, wherein the sensor control device receives the first instructions to enter into the programming mode prior to causing the first storage block of the first set of storage blocks to be marked as inaccessible.

10. The sensor control device of claim 1, wherein one of the first communication protocol and the second communication protocol is Bluetooth Low Energy and one of the first communication protocol and the second communication protocol is near-field communication.

11. The sensor control device of claim 1, wherein the one or more processors are further configured to perform one or more integrity checks of the memory prior to executing the second instructions of the program data written to the second storage block.

12. The sensor control device of claim 11, wherein the one or more integrity checks comprise performing an integrity check on each storage block of the second set of storage blocks.

13. The sensor control device of claim 1, further comprising a rewriteable memory communicatively coupled to the one or more processors, the first communication module, the second communication module, and the glucose sensor, wherein the program data written to the second storage block are first written to the rewriteable memory.

14. The sensor control device of claim 13, wherein the one or more processors execute the second instructions of the program data written in storage blocks of the second set of storage blocks based on a profile stored in the rewriteable memory.

15. The sensor control device of claim 14, wherein causing the first storage block of the first set of storage blocks to be marked as inaccessible comprises modifying the profile stored in the rewriteable memory.

16. The sensor control device of claim 1, wherein the sensor control device is configured to, prior to causing the first storage block of the first set of storage blocks to be marked as inaccessible, re-initialize into an update-compatible state.

17. The sensor control device of claim 1, wherein the glucose sensor is configured to generate glucose data, wherein the glucose data is indicative of levels of glucose in a fluid of a patient; and wherein processing the glucose data received from the glucose sensor comprises:
analyzing the glucose data using the program data written to the storage blocks of the second set of storage blocks; and
transmitting the glucose data to an external device using the first communication module or the second communication module.

18. A method comprising:
receiving, by one or more processors of a sensor control device using a first communication module of the sensor control device communicatively coupled with the one or more processors, first instructions that instruct the one or more processors to enter into a programming mode to write program data to a second storage block of a second set of storage blocks of a memory, wherein the first instructions are signed with a first digital signature token generated based on information associated with a manufacturer of the sensor control device, wherein the memory is a one-time programmable memory and comprises a plurality of storage blocks, the plurality of storage blocks including a first set of storage blocks that have been written into and are in a non-programmable state and the second set of storage blocks that have not been written into and are in a programmable state, wherein the first communication module is compatible with a first communication protocol;
validating the first instructions based on the first digital signature token generated based on information associated with the manufacturer of the sensor control device;
subsequent to validating the first instructions based on the first digital signature token, entering into the programming mode;
receiving, by the one or more processors using a second communication module of the sensor control device, the program data, wherein the second communication module is compatible with a second communication protocol, wherein the program data is signed with a second digital signature token generated based on information associated with the manufacturer of the sensor control device;
validating the program data based on the second digital signature token generated based on information associated with the manufacturer of the sensor control device, wherein the first digital signature token is different from the second digital signature token;
subsequent to validating the program data based on the second digital signature token, writing, by the one or more processors, the program data to the second storage block from the second set of storage blocks that are in the programmable state, and causing the second storage block to be placed into the non-programmable state;
writing, by the one or more processors, marking data to the memory to mark a first storage block from the first set of storage blocks that are in the non-programmable state as inaccessible; and
processing, by the one or more processors, data received from a glucose sensor based on executing second instructions stored in the program data written to the second storage block.

19. A computer-readable non-transitory storage media comprising a set of instructions that are configured, when executed by one or more processors of a sensor control device, to perform operations comprising:
receiving, by the one or more processors using a first communication module of the sensor control device communicatively coupled with the one or more processors, first instructions that instruct the one or more processors to enter into a programming mode to write program data to a second storage block of a second set of storage blocks of a memory, wherein the first instructions are signed with a first digital signature token generated based on information associated with a manufacturer of the sensor control device, wherein the memory is a one-time programmable memory and comprises a plurality of storage blocks, the plurality of storage blocks including a first set of storage blocks that have been written into and are in a non-programmable state and the second set of storage blocks that have not been written into and are in a programmable state, wherein the first communication module is compatible with a first communication protocol;
validating the first instructions based on the first digital signature token generated based on information associated with the manufacturer of the sensor control device;
subsequent to validating the first instructions based on the first digital signature token, entering into the programming mode;
receiving, by the one or more processors using a second communication module of the sensor control device, the program data, wherein the second communication module is compatible with a second communication protocol, wherein the program data is signed with a second digital signature token generated based on information associated with the manufacturer of the sensor control device, wherein the first digital signature token is different from the second digital signature token;
validating the program data based on the second digital signature token generated based on information associated with the manufacturer of the sensor control device;
subsequent to validating the program data based on the second digital signature token, writing, by the one or more processors, the program data to the second storage block from the second set of storage blocks that are in the programmable state, and causing the second storage block to be placed into the non-programmable state;
writing, by the one or more processors, marking data to the memory to mark a first storage block from the first set of storage blocks that are in the non-programmable state as inaccessible; and
processing, by the one or more processors, data received from a glucose sensor based on executing second instructions stored in the program data written to the second storage block.

* * * * *